United States Patent
Katayama et al.

(10) Patent No.: US 10,511,952 B2
(45) Date of Patent: Dec. 17, 2019

(54) EMERGENCY DETERMINATION SUPPORT SYSTEM, AND A NON-TRANSITORY COMPUTER READABLE MEDIUM HAVING STORED THEREON AN EMERGENCY DETERMINATION SUPPORT PROGRAM

(71) Applicant: OSAKA UNIVERSITY, Osaka (JP)

(72) Inventors: Yusuke Katayama, Osaka (JP); Yasumitsu Mizobata, Osaka (JP); Sumito Hayashida, Osaka (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 16/081,903

(22) PCT Filed: Mar. 2, 2017

(86) PCT No.: PCT/JP2017/008209
§ 371 (c)(1),
(2) Date: Sep. 1, 2018

(87) PCT Pub. No.: WO2017/154711
PCT Pub. Date: Sep. 14, 2017

(65) Prior Publication Data
US 2019/0069155 A1    Feb. 28, 2019

(30) Foreign Application Priority Data
Mar. 7, 2016   (JP) .................. 2016-043594

(51) Int. Cl.
*H04M 11/04*    (2006.01)
*G06Q 99/00*    (2006.01)
(Continued)

(52) U.S. Cl.
CPC ............. *H04W 4/90* (2018.02); *G16H 10/60* (2018.01); *G16H 50/30* (2018.01); *G16H 80/00* (2018.01); *H04M 11/04* (2013.01)

(58) Field of Classification Search
CPC .......... H04W 4/90; G16H 10/60; G16H 50/30
(Continued)

(56) References Cited

U.S. PATENT DOCUMENTS

2013/0222133 A1* 8/2013 Schultz ................ G08G 1/205
                                                 340/539.13
2014/0365390 A1* 12/2014 Braun ................. G06Q 50/265
                                                 705/325
(Continued)

FOREIGN PATENT DOCUMENTS

JP    2004-145671 A    5/2004
JP    2007-094935 A    4/2007
(Continued)

OTHER PUBLICATIONS

English translation of Japanese Patent Application Publication No. JP 2007-172275 from Espacenet.com (pub. date Jul. 5, 2007).*
(Continued)

*Primary Examiner* — Rafael Pérez-Gutiérrez
*Assistant Examiner* — Mark G. Pannell
(74) *Attorney, Agent, or Firm* — Renner, Otto, Boisselle & Sklar, LLP

(57) ABSTRACT

A program that supports emergency determination with an information terminal (1) equipped with a display (11) and a touch panel (12). The program makes the information terminal function as: an input reception unit (102) configured to receive input of age and sex on an injured or ill person through the touch panel (12); the input reception unit (102) configured to display a plurality of symptoms on the display (11) to allow a user to select any symptom from the plurality of symptoms through the touch panel (12), and an emergency determination unit (103) configured to determine the level of emergency degree corresponding to the age and the sex of the injured or ill person and the selected symptom and
(Continued)

display the emergency degree on the display (11). This enables determination of the emergency degree of symptoms as well as notification of the determined emergency degree to the individual using an information terminal owned by the individual.

6 Claims, 37 Drawing Sheets

(51) Int. Cl.
    *G06Q 10/00* (2012.01)
    *G06Q 50/00* (2012.01)
    *H04W 4/90* (2018.01)
    *G16H 10/60* (2018.01)
    *G16H 50/30* (2018.01)
    *G16H 80/00* (2018.01)

(58) Field of Classification Search
    USPC ................................................ 455/404.1
    See application file for complete search history.

(56) References Cited

U.S. PATENT DOCUMENTS

2016/0070874 A1* 3/2016 Cosentino .............. G16H 10/20
                                                                   705/2
2016/0285800 A1* 9/2016 Qian ..................... G06F 19/3418
2017/0161370 A1* 6/2017 Endo ...................... G06T 11/206

FOREIGN PATENT DOCUMENTS

| | | |
|---|---|---|
| JP | 2007-172275 A | 7/2007 |
| JP | 2009-086766 A | 4/2009 |
| JP | 2010-232963 A | 10/2010 |
| JP | 2013-092930 A | 5/2013 |
| JP | 2013-148996 A | 8/2013 |
| JP | 2015-141709 A | 8/2015 |
| WO | 2013/065113 A | 5/2013 |

OTHER PUBLICATIONS

International Search Report for corresponding App. No. PCT/JP2017/008209, dated May 16, 2017.

Yusuke Katayama, "Development of system (ORION) to support emergency transportation and collect information using smartphones", Journals of Japanese Society for Emergency Medicine, vol. 16, p. 288, published in Jun. 2013 (discussed in Specification).

EMS app service launched, Osaka Municipal Fire Department: Input symptoms to determine urgency, Sankei Newspaper issued on Sep. 9, 2015.

* cited by examiner

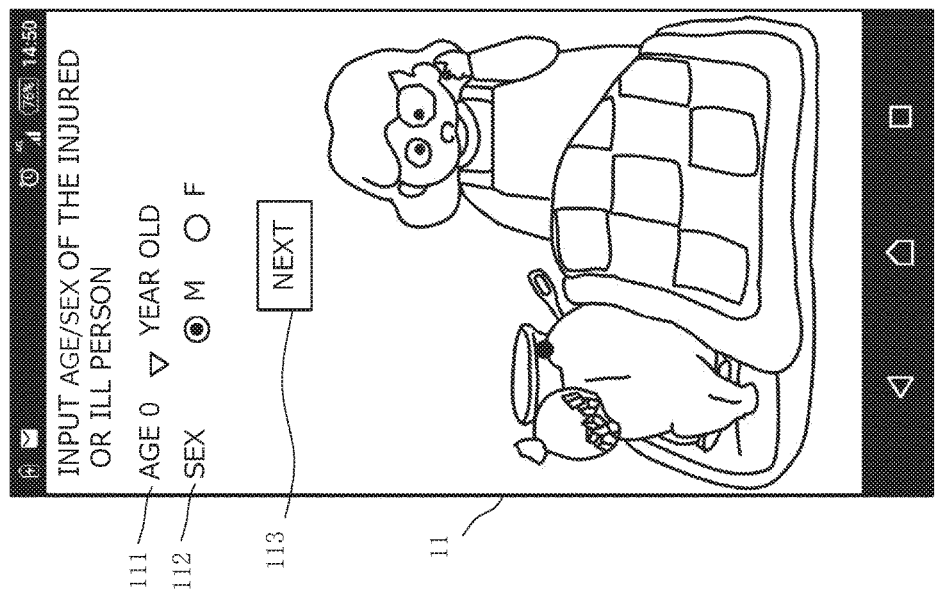

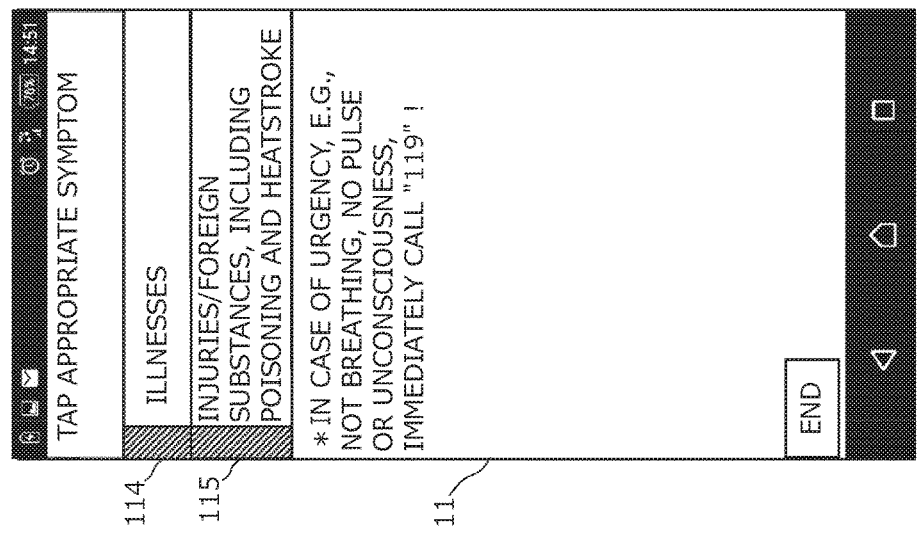

Fig. 7B

- TAP APPROPRIATE SYMPTOM
- TRAUMA OF HEAD OR NECK
- INJURY OR FOREIGN SUBSTANCES IN EYES
- INJURY OR FOREIGN SUBSTANCES IN EARS
- FOREIGN SUBSTANCES IN NOSE
- EATING CIGARETTES
- SWALLOWING SOLID FOREIGN SUBSTANCES
- DRINKING LIQUID FOREIGN SUBSTANCES
- HEAT STROKE
- INJURY IN ARMS/LEGS OR FACE
- PROBLEM IN HANDS OR ARMS
- RETURN

123 — INJURIES/FOREIGN SUBSTANCES, INCLUDING POISONING AND HEATSTROKE

11

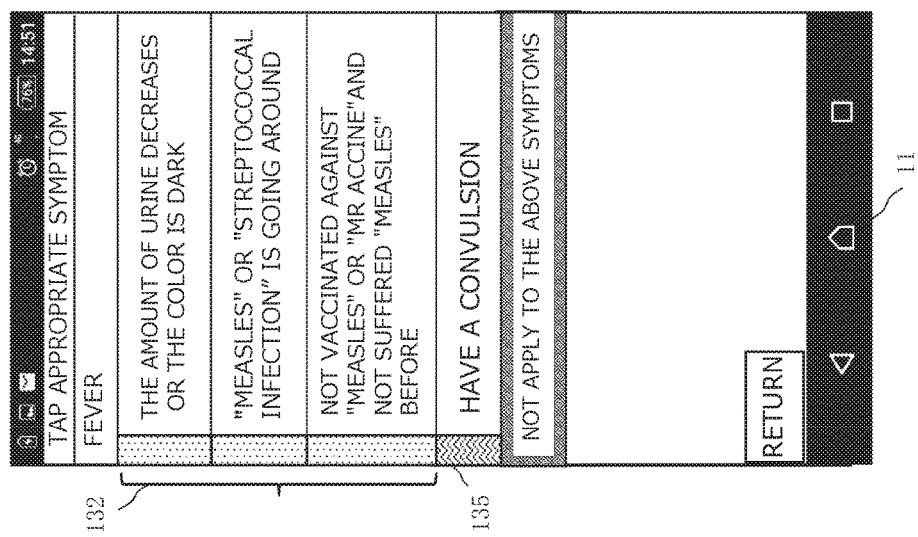

Fig. 8C

TAP APPROPRIATE SYMPTOM

FEVER

- HAVING A FEVER LESS THAN 41 DEGREES, BUT DIDN'T GO TO HOSPITAL
- HAVING WET COUGH, AND YELLOWISH OR GREENISH RUNNY NOSE
- EARS SEEM TO HURT
- HAVING PUS FROM EAR OR RUNNY EAR
- SEEMS TO HAVE PAIN DURING URINATION
- GETTING RED ALL OVER THE BODY OR HAVING BUMPS LIKE HIVES

NOT APPLY TO THE ABOVE SYMPTOMS

RETURN 133
136
11

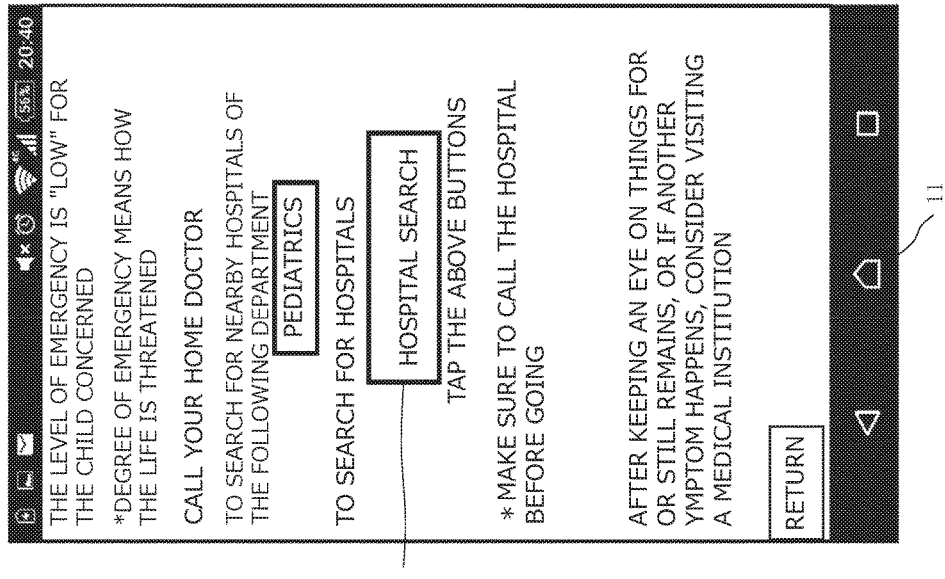

Fig. 10B

TAP APPROPRIATE SYMPTOM

TRAUMA OF HEAD OR NECK

HAVING A FEVER OF 38 DEGREES OR MORE

HAD BLEEDING, BUT STOPPED BY APPLYING PRESSURE THERE

WAS TOLD BY DOCTOR TO HAVE BLEEDING DIATHESIS OR DIFFICULTY IN STOP BLEEDING

VOMITED ONCE, BUT BACK TO NORMAL AFTER THAT

HAVING A BIG BUMP BUT OTHERS ARE AS USUAL

NOT APPLY TO THE ABOVE SYMPTOMS, BUT LESS THAN THREE MONTHS AFTER BIRTH

NOT APPLY TO THE ABOVE SYMPTOMS

RETURN

152

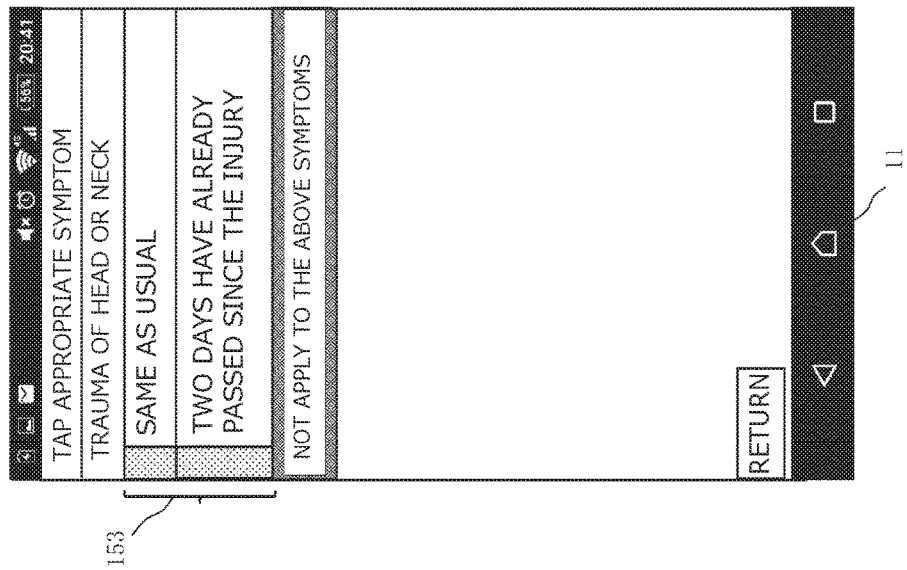

Fig. 19

THIS IS THE QUESTIONNAIRE YOU AGREED TO ANSWER THE OTHER DAY. TELL US THE DETAILS ABOUT THAT DAY.

Q1 : DID YOU VISIT HOSPITAL OR CLINIC?

1. VISITED HOSPITAL DISPLAYED ON APP
2. VISITED ANOTHER HOSPITAL (INCLUDING HOME DOCTOR)
3. NOT VISITED
4. THE DISPLAYED HOSPITAL DECLINED, AND SO REQUESTED AMBULANCE
5. KEPT AN EYE ON THINGS AT HOME
6. VISITED THE HOSPITAL THE NEXT DAY

RETURN

Fig. 20

Q2 : WHAT HAPPENED AFTER VISITING HOSPITAL OR CLINIC?

1. TREATED AS OUTPATIENT AND WENT HOME
2. HOSPITALIZED
3. THEY DECLINED THE TREATMENT AND CHANGED HOSPITAL

RETURN

Fig. 21

Q3 : WHY DIDN'T YOU VISIT HOSPITAL?

1. YOU HAD NO MEANS FOR TRANSPORTATION

2. YOU JUDGED YOU COULD WAIT UNTIL NEXT DAY OR LATER TO VISIT THE HOSPITAL (INCLUDING THE CASE THAT YOU WERE TOLD AS SUCH BY DOCTOR)

3. YOU WERE REFERRED TO ANOTHER HOSPITAL

4. THEY DECLINED THE TREATMENT

5. YOU COULDN'T GET THROUGH TO THE HOSPITAL

RETURN

EMERGENCY DETERMINATION SUPPORT SYSTEM, AND A NON-TRANSITORY COMPUTER READABLE MEDIUM HAVING STORED THEREON AN EMERGENCY DETERMINATION SUPPORT PROGRAM

TECHNICAL FIELD

The present invention relates to techniques for supporting emergency determination to support the emergency activity in accordance with the emergency degree of injured or ill persons.

BACKGROUND ART

Although the number of emergency transportations has been increased recently, there is a declining trend of the number of designated emergency hospitals. This lengthens the time required to select hospitals during emergency transportation, and the measures to correct the situation have been requested. Patent Literature 1, for example, describes an emergency support system including a computer terminal carried by an emergency medical staff and a main server. When the emergencymedical staff inputs the symptoms of the emergency patient with the computer terminal and transmits the data to the main server, then the main server selects a hospital that can accept the patient based on the received symptoms of the emergency patient and information on the designated emergency hospitals, and notifies the computer terminal about the hospital, so as to transport the patient quickly. Patent Literature 2 describes another emergency support system that provides an application for primary care about emergency case that is installed beforehand in a smartphone owned by an injured or ill person. At the onset of the symptom, information on the patient is transmitted to the medical institution via network by means of a camera and a microphone of the smartphone, whereby a doctor can inspect the patient until the ambulance arrives to the site.

As one of the reasons for the increasing tendency of the number of requests for emergency transportation, an injured or ill person or their family cannot determine the emergency degree of the symptoms. The emergency support systems described in Patent Literatures 1 and 2 are for rapid emergency medical care of a patient using a mobile terminal. They are not intended to support the emergency determination on the symptoms by an injured or ill person or their family.

Medical algorithm to determine the emergency degree of an injured or ill person has been typically used by medical institutions. For instance, in Canada, they have developed and operated a system to determine (triage) the emergency degree of outpatients at hospital, named CTAS (Canadian Triage & Acuity Scale) since 1998. Based on this CTAS, the system in the Japanese version named JTAS (Japan Triage & Acuity Scale) also has been developed and operated in Japan.

Non-Patent Literature 1 shows that they developed an application named ORION (Osaka emergency information Research Intelligent Operation Network system) to search for hospitals based on the practice standard of transportation. This literature describes a system to allow emergency medical staffs to reflect the details of the transportation to hospitals on the application using their smartphones to support the selection of a suitable hospital depending on the situation.

CITATION LIST

Patent Literature

Patent Literature 1: WO2013/65113
Patent Literature 2: Japanese Patent Application Laid-Open No. 2015-141709

Non Patent Literature

[Non-Patent Literature 1] "Development of system (ORION) to support emergency transportation and collect information using smartphones", Yusuke KATAYAMA, Journals of Japanese Society for Emergency Medicine, vol. 16, p 288, published in June, 2013.

SUMMARY OF INVENTION

Technical Problem

The emergency determination in accordance with CTAS or JTAS is operated in a paper-based manner. To verify the appropriateness of such medical algorithm, the paper-based data has to be collected and analyzed. Practically, however, such verification has not been conducted because of its large amount of data. Since it is not practical for ordinary people to always carry such paper-based criteria for determination on emergency (e.g., a special form for the purpose), the public-based operation of such emergency determination also has not started.

The ORION that is an application to search for hospitals described in Non-Patent Literature 1 is to support the determination on injured or ill persons by an emergency medical team for their smooth selection of medical institutions. This application is not configured to utilize information terminals owned by individuals.

In view of the above, the present invention proposes an emergency determination supporting system and a program that determine the emergency degree of symptoms and shows the determined emergency degree using information terminals owned by individuals.

Solution to Problem

A program according to the present invention supports emergency determination with an information terminal equipped with a display and an operating unit. The program makes the information terminal function as: an injured/ill person information reception means configured to receive input of attribute information on an injured or ill person through the operating unit of the information terminal; a symptom selection means configured to display a plurality of symptoms on the display of the information terminal to allow a user to select any symptom from the plurality of symptoms through the operating unit; and an emergency determination means configured to determine an emergency degree corresponding to the attribute information and the selected symptom and notify the emergency degree to the user.

According to the present invention, after receiving the input of attribute information on an injured or ill person through the operating unit of the information terminal (mobile terminal), such as a smartphone, owned by a user as an individual, the display of the information terminal displays a plurality of symptoms. Then the user selects a symptom corresponding to the injured or ill person from the displayed symptoms via the operating unit. When receiving a selection of the symptom, the information terminal determines the emergency degree corresponding to the input attribute information on the injured or ill person and the selected symptom, and shows an image, for example, of the result on the display. In this way, when the user inputs the attribute information on the injured or ill person and selects a current symptom, the user can personally understand the emergency degree automatically and rapidly. This inhibits non-urgent request for ambulance, which therefore can lead to proper dispatching of ambulance, and can contribute to shortening the arrival time of ambulance. In one aspect, the number of selected symptoms may be one or more.

An emergency determination supporting system according to the present invention includes: a first server configured to receive, from an information terminal configured to receive, as an emergency case, attribute information on an injured or ill person and information on selected symptoms and determine a level of emergency degree for the received information and equipped with a calling function and a communication function, the attribute information, the received symptoms and information on emergency degree for each emergency case; and a second server configured to, when the information terminal determines the emergency degree as a high level, and when a user makes a call to the emergency calling phone via the calling function for emergency transportation of the injured or ill person, receive pre-hospital activity information including information on the injured or ill person and pre-hospital activity information including information on the injured or ill person. One of the first server and the second server includes: a joining means configured to check the attribute information received by the first server against the information on the injured or ill person received by the second server to join the emergency case; and an emergency analysis means configured to statistically evaluate and analyze a relationship between symptoms and the level of emergency degree for each of the joined emergency cases.

An emergency determination supporting method according to the present invention include a first reception step in which a first server receives, from an information terminal configured to receive, as an emergency case, attribute information on an injured or ill person and information on selected symptoms and determine a level of emergency degree of the received information, and equipped with a calling function and a communication function, the attribute information, the received symptoms and information on emergency degree for each emergency case; a second reception step in which when the information terminal determines the emergency degree as a high level, and when a user makes a call to the emergency calling phone via the calling function for emergency transportation of the injured or ill person, a second server receives pre-hospital activity information including information on the injured or ill person and pre-hospital activity information including information on the injured or ill person; a joining step of checking the attribute information received by the first server against the information on the injured or ill person received by the second server to join each emergency case; and an analysis step of performing statistical evaluation and analysis about a relationship between symptoms and the level of emergency degree for each of the joined emergency cases.

According to the present invention as stated above, the attribute information on an injured or ill person, information on the selected symptoms and the determined emergency degree from the information terminal can be jointed with the pre-hospital activity information and the post-transportation progress information for each emergency case. Thereby when a symptom is determined as a high-level of emergency by the information terminal, such determination can be evaluated and analyzed based on the medical care performed on the emergency medical service side, and so the appropriateness of the determination can be verified. For instance, although a certain symptom is determined as high-level of emergency by information terminals in a plurality of cases, such a symptom may not be considered as high-level of emergency and the patient may receive the corresponding medical care based on the pre-hospital activity information and the post-transportation progress information. When information on the cases via the emergency consultation phone is fed back later to the second server, the emergency determination can be evaluated also for such cases that are not at a high level in emergency.

Advantageous Effects of Invention

The present invention enables determination of the emergency degree of symptoms as well as notification of the determined emergency degree to the individual using an information terminal owned by the individual.

BRIEF DESCRIPTION OF DRAWINGS

FIG. 6A is a home screen after the activation of the emergency support application.

FIG. 6B shows a screen for selection between injuries and illnesses.

FIG. 7B shows the screen following the selection of an "injury/foreign substances" button.

FIG. 8B shows the screen following the selection of a "fever" button, showing symptoms when the emergency degree is at a medium level.

FIG. 8C shows the screen following the selection of a "fever" button, showing symptoms when the emergency degree is at a low level.

FIG. 9C shows the screen following the selection of a "convulsion" button, showing the screen to search for hospitals.

FIG. 10B shows the screen following the selection of a "trauma of head or neck" button, showing symptoms when the emergency degree is at a medium level.

FIG. 10C shows the screen following the selection of a "trauma of head or neck" button, showing symptoms when the emergency degree is at a low level.

FIG. 19 shows one example of the screen of question Q1 in the questionnaire.

FIG. 20 shows one example of the screen of question Q2 in the questionnaire.

FIG. 21 shows one example of the screen of question Q3 in the questionnaire.

DESCRIPTION OF EMBODIMENTS

Figure 1:
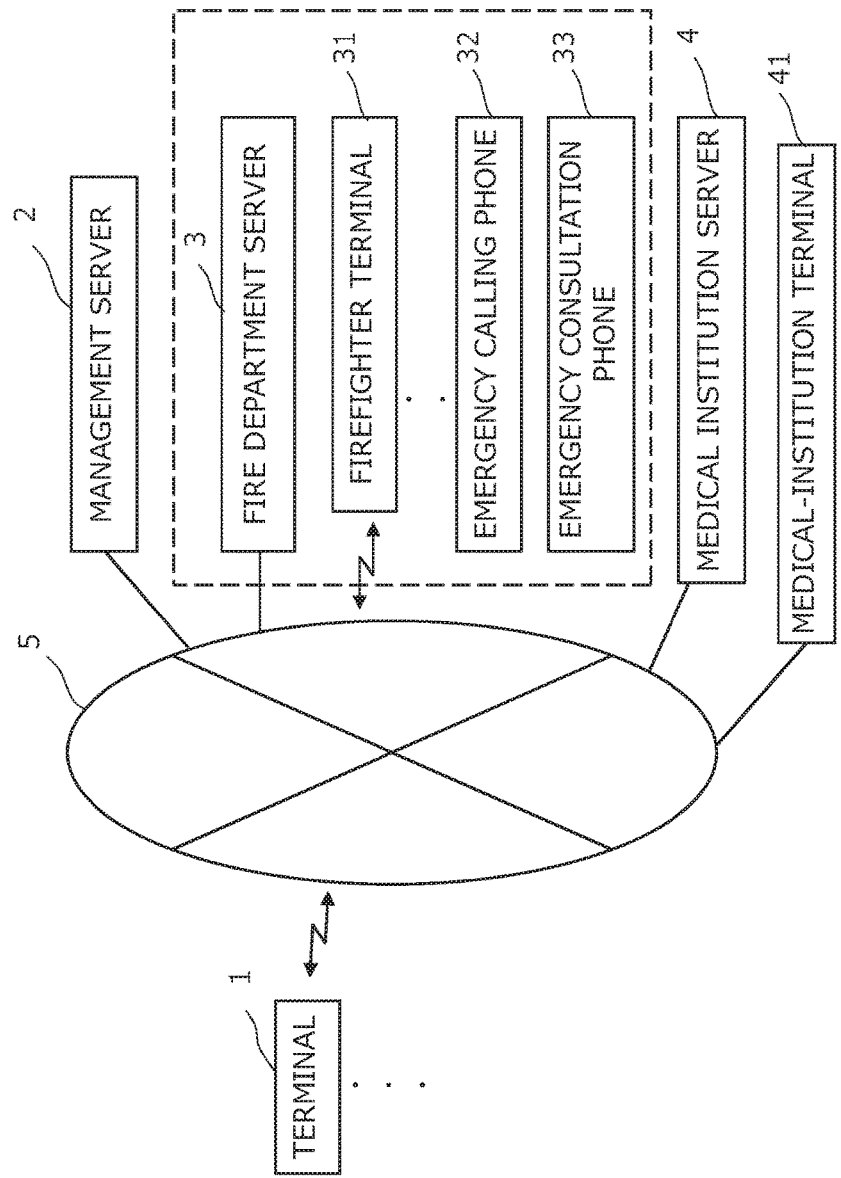
FIG. 1 schematically shows the configuration of a network communication system including an emergency determination supporting system according to the present invention.

FIG. 1 schematically shows the configuration of a network communication system including an emergency determination supporting system according to the present invention. The network communication system in FIG. 1 includes a network 5, such as the internet, to which the terminal 1 can connect. To the network 5, devices other than the terminal 1 also connect communicably via the internet service provider, and they include a management server 2, a fire department server 3, a medical institution server 4, a firefighter terminal 31 and a medical-institution terminal 41. Note here that the firefighter terminal 31 and the medical-institution terminal 41 in another mode may connect to the fire department server 3 and the medical institution server 4, respectively, via their LAN (Local Area Network). The management server 2 makes up a first server, and the fire department server 3 and the medical institution server 4 make up a second server.

The terminal 1 is owned by an ordinary people. The terminal 1 internally includes a computer as described later, and has a function of inputting and processing information and a function for calling and other communications. Preferably the terminal 1 is a mobile terminal, such as a smartphone. Such a mobile terminal enables emergency information transmission (calling and other communications) from the site if they are injured or have illness outdoors, typically when they are away from home.

The management server 2 stores an application program (hereinafter called an emergency support application) necessary to execute the emergency determination support and the related data. The management server 2 is described later in details. The management server 2 also stores a program to execute emergency analysis processing and questionnaire management processing relating to the emergency support application. The fire department server 3 and the medical institution server 4 function as a database. In the present embodiment, these servers function as an emergency medical care database. The fire department server 3 is managed by a fire department located at an area where the emergency determination supporting system is operated. The medical institution server 4 is managed by each medical institution located at an area where the emergency determination supporting system is operated, and this server 4 is described later in details. The present system can be applied to a mode that covers a plurality of fire-fighting headquarters or the area throughout the country as well, which will be described later.

The firefighter terminal 31 is a mobile terminal (e.g., a tablet-type computer) owned by firefighters. The firefighter terminal 31 has a function of inputting personal information on an injured or ill person (e.g., name, age, and sex) and on the pre-hospital activity, such as determinations on the symptoms (e.g., the dispatch destination, the date and time of transportation, background of the patient, the result of observation of the patient, and the process to select the hospital for transportation) as well as a communication function with at least the fire department server 3. The firefighter terminal 31 is not limited to a mobile terminal, which may be a terminal installed at the fire department if they enable the inputting of information on the pre-hospital activity and the communications.

The medical-institution terminal 41 is a personal computer, for example, that is installed at each medical institution or is of a mobile (tablet) type. The medical-institution terminal 41 has a function of inputting personal information on an injured or ill person (e.g., name, age, and sex) and on the progress after transportation (e.g., the date and time of transportation, the name of disease by definitive diagnosis, the progress of treatment, and transcription) as well as a communication function with at least the medical institution server 4. As is known, a mobile terminal, such as the terminal 1 and the firefighter terminal 31, can communicate with a server over the network 5 via a wireless LAN, such as Wi-Fi.

An emergency calling phone 32 is installed at a fire department, and has a specific telephone number assigned for emergency. When receiving a call with the emergency calling phone, firefighters are dispatched for emergency operations. An emergency consultation phone 33 is installed at a fire department, for example, and has a specific telephone number assigned for emergency consultation. This emergency consultation phone 33 provides a service to an injured or ill person (or their family) so that they can talk with a medical expert for consultation about their symptoms of the injury or illness.

Figure 2:
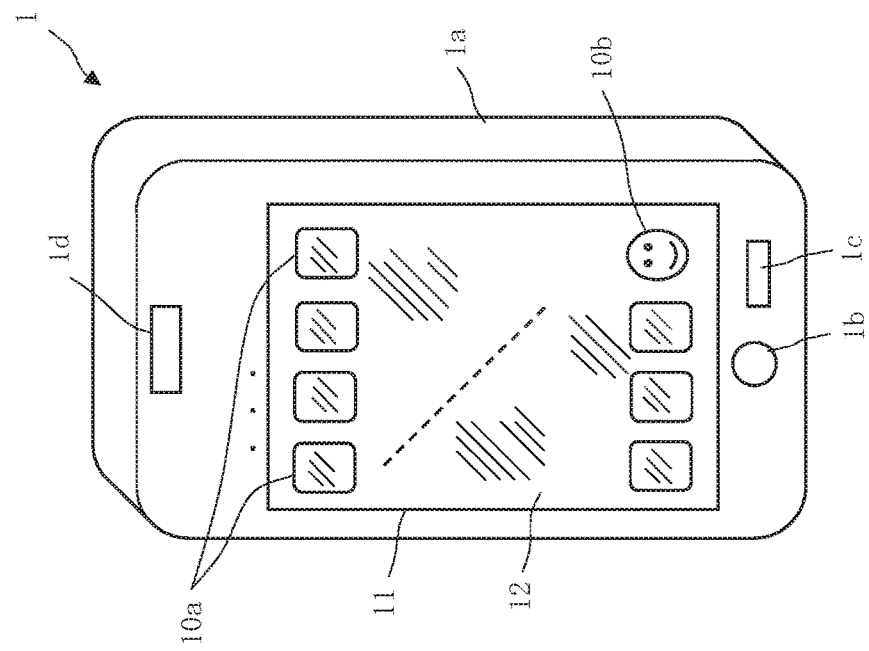
FIG. 2 is a perspective view of a terminal.

FIG. 2 is a perspective view of the terminal 1. The present embodiment includes a smartphone as the terminal 1. A smartphone is a mobile phone that internally includes a computer and has a function of calling as well as a data inputting/processing function. The smartphone can connect to the internet, for example, to execute functions for email or browsing and be communicable with a server in the net. The terminal 1 has a plate-like casing 1a, and a display 11 of a necessary size is disposed on the substantially entire face of the front face of the casing. The display 11 displays images, and may be a liquid crystal panel, a plasma display panel, or an organic EL (Electro-Luminescence) device. A transparent or translucent touch panel 12 is stacked on the display 11. The tough panel 12 functions as an operating unit to detect a contact operation to the panel as a signal indicating the coordinates at the contact position.

On the display surface, a plurality of icons 10a, . . . 10b having corresponding designs are displayed at the set coordinate positions, and these icons are associated with various types of application (AP) programs. Each application (AP) program is loaded from a site selling applications on the network, for example, by downloading, and is stored in the terminal 1. Such an application program is then shown on the display in the form of a corresponding shortcut icon.

The coordinates of the icons on the display 11 are associated with the coordinates of the contact position, whereby the terminal can detect which one of the icons 10a, . . . 10b is designated for selection via the touchpanel 12. The applications corresponding to the icons 10a may implement an email function, a browsing function, a music distribution function and the like. When the user designates anyone of the icons 10a, the corresponding application activates. Such plurality of icons includes an icon 10b that is associated with the emergency support application to which the present invention relates. The icon 10b indicates that the emergency support application has been loaded by downloading it from the management server 2 or acquiring it through a site selling applications on the network. As described later, automatic updating of the emergency support application may be instructed beforehand. Then the latest program can be always installed every time the emergency support application is updated.

At the bottom of the casing 1a, the terminal 1 has a power switch 1b to activate and deactivate the terminal and a microphone 1c for call. At the top of the casing 1a, the terminal has a speaker 1d for call. The casing 1a internally includes a positioning device 13 (see FIG. 3), such as a GPS (Global Positioning System) receiver.

Figure 3:
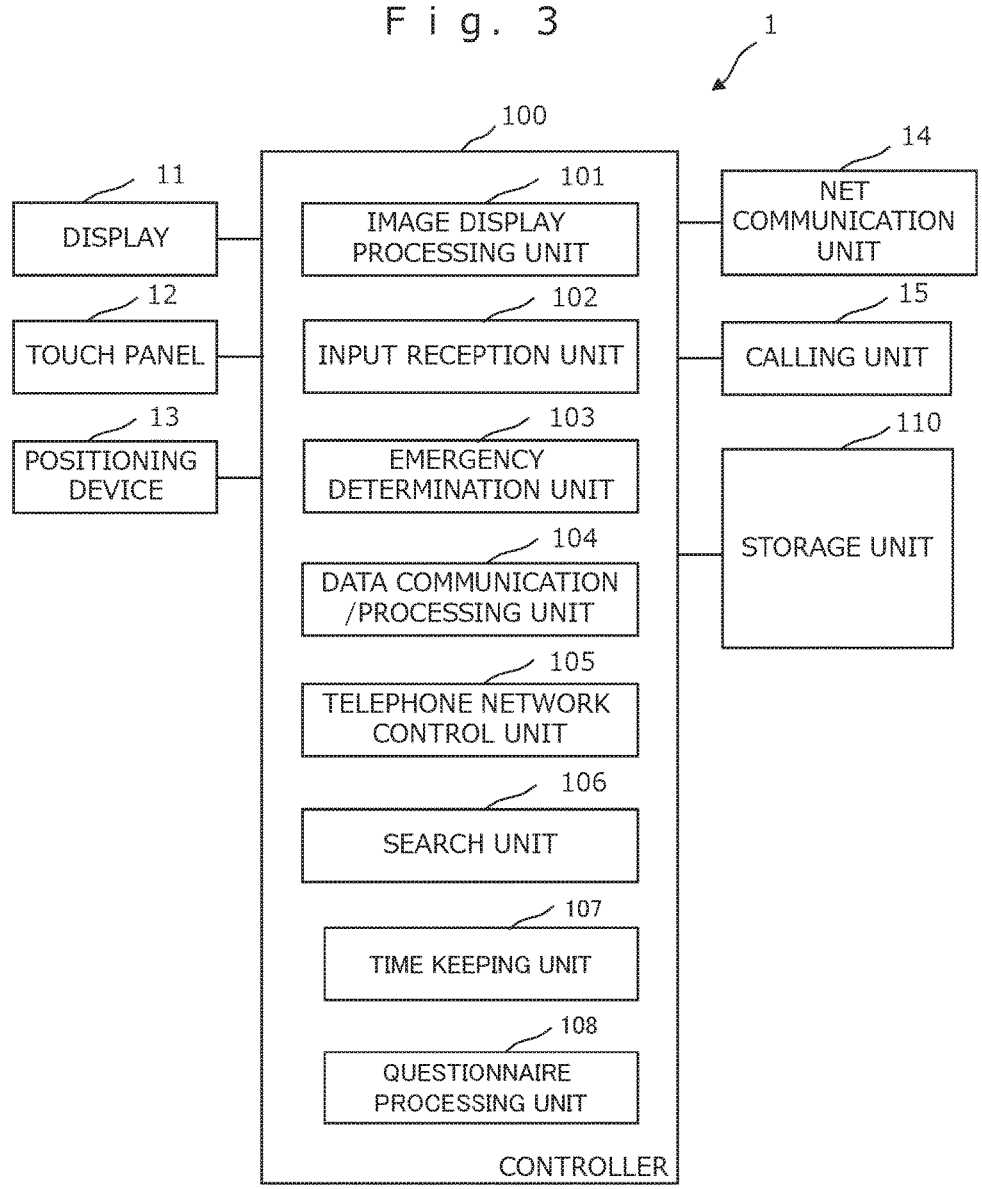
FIG. 3 is a functional block diagram of the terminal.

FIG. 3 is a functional block diagram of the terminal 1. The terminal 1 includes a controller 100 made up of a computer. The controller 100 connects to a storage unit 110. The controller also connects to the display 11, the touch panel 12 and the positioning device 13 as well as a net communication unit 14 and a calling unit 15.

The storage unit 110 stores various types of control programs that allow the terminal 1 to execute various functions of calling, information inputting/processing and communications. The storage unit has a work area as well to temporarily store the information during processing. More specifically the storage unit 110 stores the emergency support application and necessary data that are downloaded from a site selling applications or the management server 2 and temporarily stores the history of operation during the inputting by an injured or ill person (or their family next to them).

The net communication unit 14 connects the terminal 1 to the management server 2 for data communication as described later during the execution of the emergency support application, at the time when the execution ends, or at a predetermined timing after the ending. The calling unit (network control unit) 15 connects the terminal 1 to other specific phones 32 and 33 via a public line during the execution of the emergency support application.

When the computer of the controller 100 executes a control program stored in the storage unit 110, the terminal 1 operates as a phone, an information inputting/processing device, and an information communication device.

The following describes the configuration and the operation when the controller 100 executes the emergency support application. More specifically when the controller 100 executes the emergency support application, it functions as an image display processing unit 101, an input reception unit 102, an emergency determination unit 103, a data communication/processing unit 104, a telephone network control unit 105, a search unit 106, a time keeping unit 107, and a questionnaire processing unit 108.

In response to the input operation with the touch panel 12, the image display processing unit 101 displays various types of images on the display 11 as shown in FIGS. 6 to 12 as well as shown in FIGS. 17 to 21.

FIG. 6A is a home screen after the activation of the emergency support application to receive attribute information on an injured or ill person. Examples of the attribute information include age 111 and sex 112, and the display also shows a next button 113 to be pushed after inputting the attribute information. For instance, the age may be input by a numeric keypad, and the sex maybe input by tapping (pressing) one of the options. FIG. 6B is a screen for selection between injuries or illness. A selection can be made by tapping one of an "illness" button 114 and an "injuries/foreign substances" button 115. The following describes the case of inputting information with the touch panel 12. In another mode based on a voice recognition technique, the information may be input through voice.

Figure 7A:
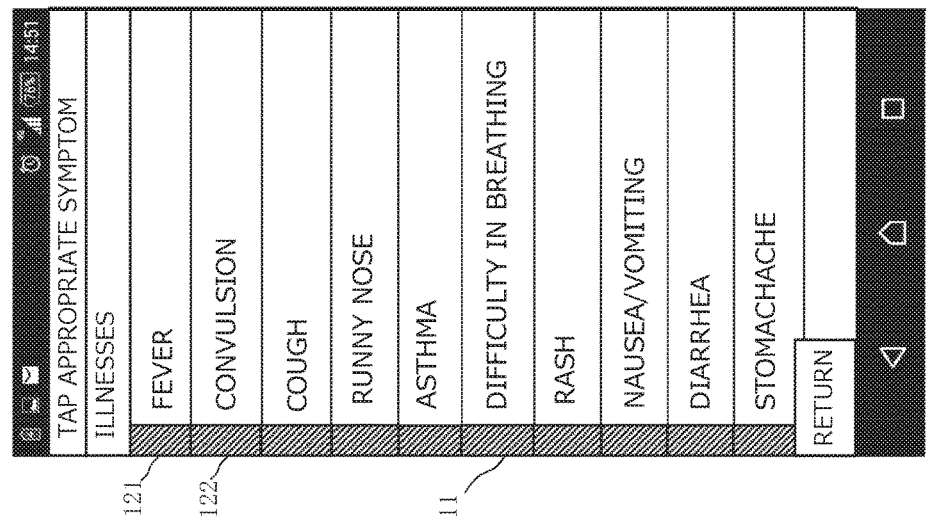
FIG. 7A shows the screen following the selection of an "illness" button.

In the present embodiment, the symptoms are configured to have two hierarchical levels and a tree-shaped structure so that they are classified from a high-level concept to a low-level concept. FIG. 7A and FIG. 7B show a screen of the symptoms at the high level (first hierarchical level), and FIGS. 8A to 8C show a screen of the symptoms at the low level (second hierarchical level).

FIG. 7A shows the screen following the selection of the "illness" button 114 (FIG. 6B), displaying a plurality of symptoms of the illness that are listed in rows. In this drawing, a "fever" button 121, a "convulsion" button 122, . . . and other buttons are displayed from the above, for example. FIG. 7B shows the screen following the selection of the "injuries/foreign substances" button 115 (FIG. 6B), displaying a plurality of symptoms of the injuries/foreign substances that are listed in rows. In this drawing, a "trauma of head or neck" button 123 is displayed at the top, for example. Pressing a "return" button at the bottom of the screen can return the screen from the current one to the previous one. Scrolling of the screen above and below by swiping allows other symptoms to be viewed.

FIGS. 8A to 10C show an example of the screen of the symptoms when the "fever" button 121, the "convulsion" button 122 or the "trauma of head or neck" button 123 is selected, for example, in FIG. 7A and FIG. 7B, showing the low-level symptoms (the second hierarchical level).

Figure 8A:
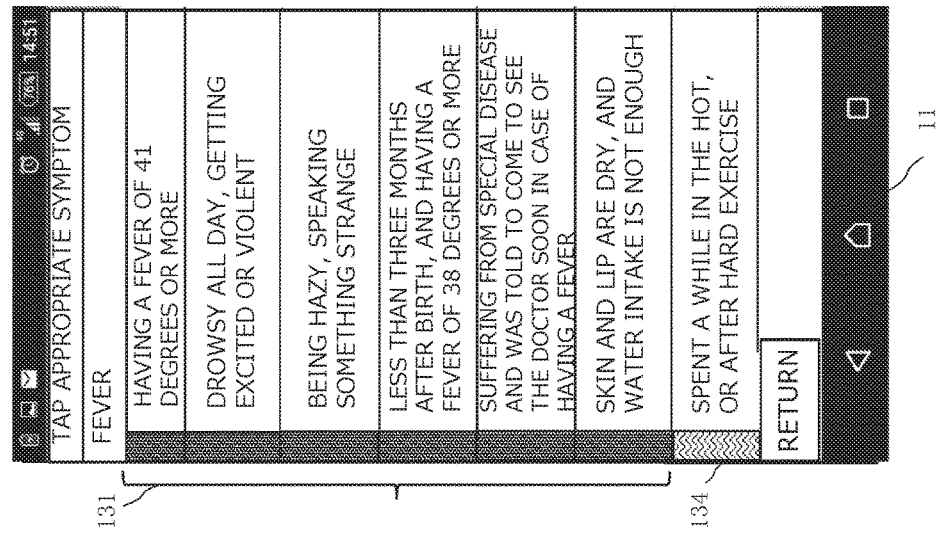
FIG. 8A shows the screen following the selection of a "fever" button, showing symptoms when the emergency degree is at a high level.

FIGS. 8A to 8C show the screens following the selection of the "fever" button 121, displaying the symptoms that are arranged in the order of a higher emergency degree from the above. The screens can be scrolled above and below among FIGS. 8A to 8C by swiping, for example. The emergency degree can be set at a plurality of levels, and three levels are set in the present embodiment. In the embodiment of FIGS. 8A to 8C, FIG. 8A shows the symptoms at a high level of emergency, and has a mark indicating a high level at the left edge of each symptom or a red mark 131 in this example. FIG. 8B shows the symptoms at a medium level of emergency, and has a mark indicating a medium level at the left edge of each symptom or a yellow mark 132 in this example. FIG. 8C shows the symptoms at a low level of emergency, and has a mark indicating a low level at the left edge of each symptom or a green mark 133 in this example. Other symptoms having marks in other colors 134, 135, 136 show that these symptoms has to shift (jump) to other symptoms at the high level (in this case, other than "fever"). This considers the following case. That is, considering the symptoms as well as the age and the sex, shifting to the other symptoms at the high level is preferable in some cases for more correct determination.

Figure 9A:
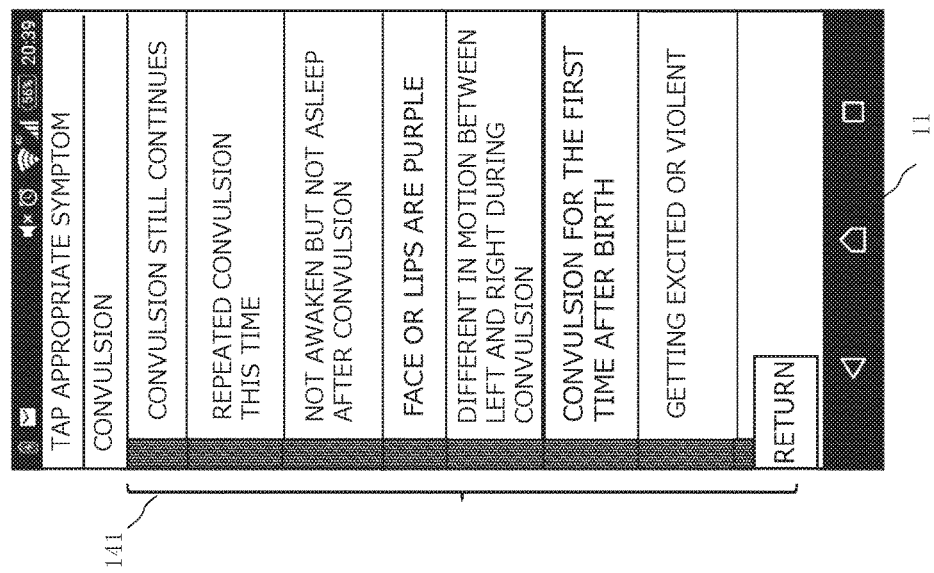
FIG. 9A shows the screen following the selection of a "convulsion" button, showing symptoms when the emergency degree is at a high level.
Figure 9B:
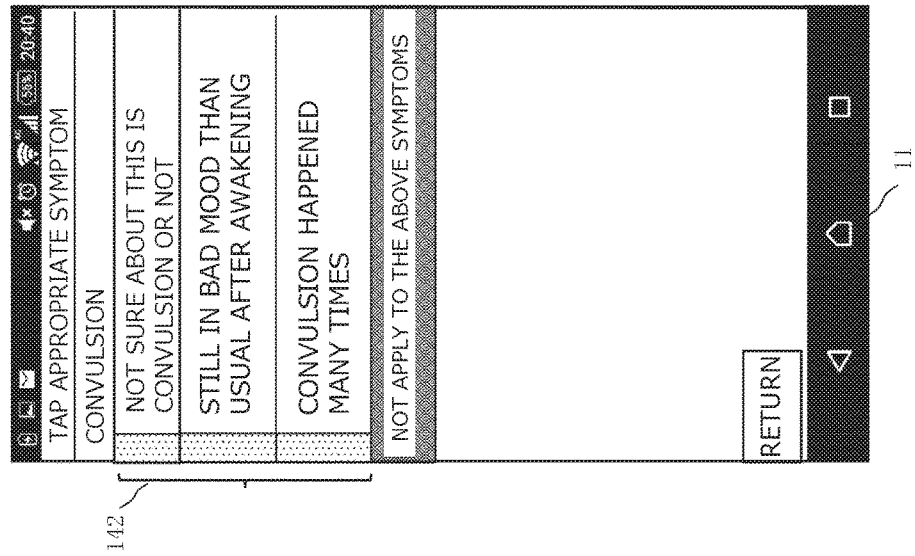
FIG. 9B shows the screen following the selection of a "convulsion" button, showing symptoms when the emergency degree is at a medium level.

FIGS. 9A to 9C show the screens following the selection of the "convulsion" button 122. FIG. 9A having a red mark 141 shows the symptoms at a high level of emergency, and FIG. 9B having a yellow mark 142 shows the symptoms at a medium level of emergency. Since the symptoms of "convulsion" are considered severer, they have only high and medium levels of emergency. A "hospital search" button 143 is displayed on the screen in this case as in FIG. 9C. The "hospital search" is described later.

Figure 10A:
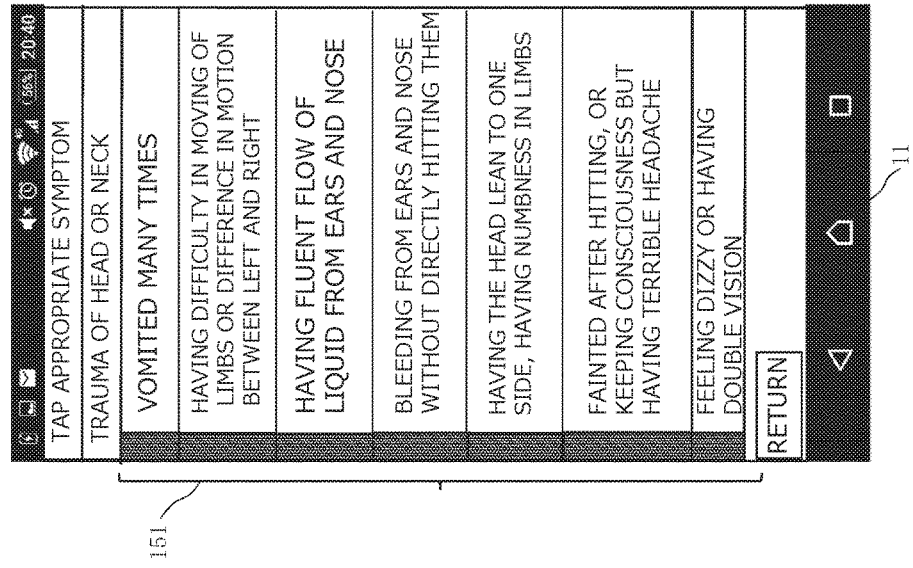
FIG. 10A shows the screen following the selection of a "trauma of head or neck" button, showing symptoms when the emergency degree is at a high level.

FIGS. 10A to 10C show the screens following the selection of the "trauma of head or neck" button 123, displaying the symptoms having a red mark 151 (FIG. 10A), a yellow mark 152 (FIG. 10B), and a green mark 153 (FIG. 10C) that are arranged in the order of emergency similarly to FIGS. 8A to 8C. Note here that the marks indicating the emergency degree in FIGS. 8A to 10C are not limited to red, yellow and green. They may be displayed in another mode other than a difference in color if the emergency degree can be visually identified. For instance, the emergency degree may be identified with graphics, or different colors or styles of the text may be used to represent the symptoms. Alternatively such identification of the emergency degree does not have to be necessarily displayed.

Figure 11A:
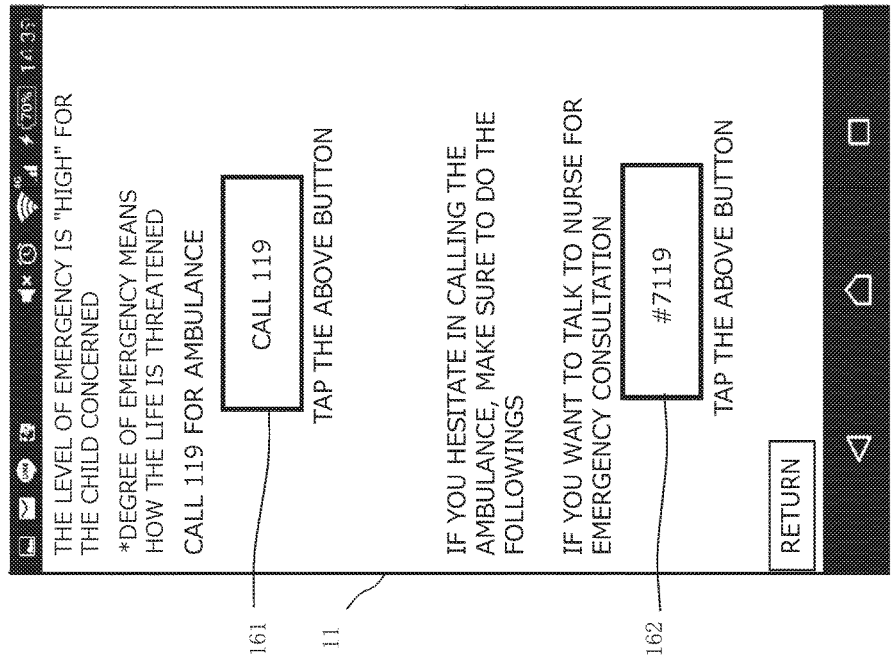
FIG. 11A shows the screen of the result corresponding to the determined emergency degree when the emergency degree is at a high level.
Figure 11B:
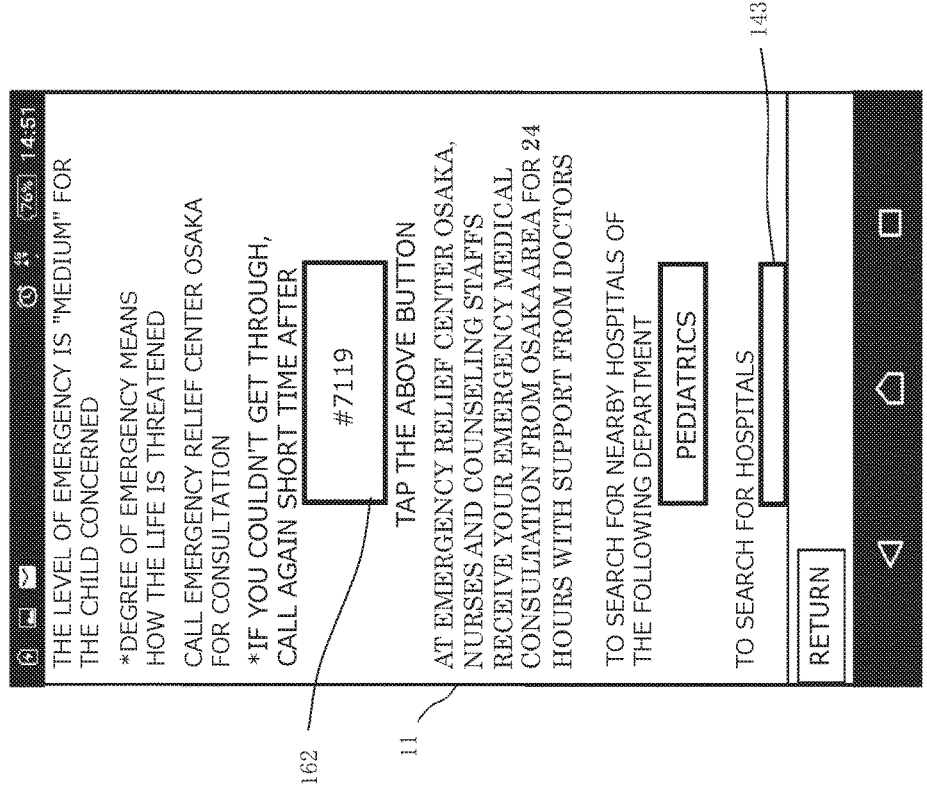
FIG. 11B shows the screen of the result corresponding to the determined emergency degree when the emergency degree is at a medium level.
Figure 11C:
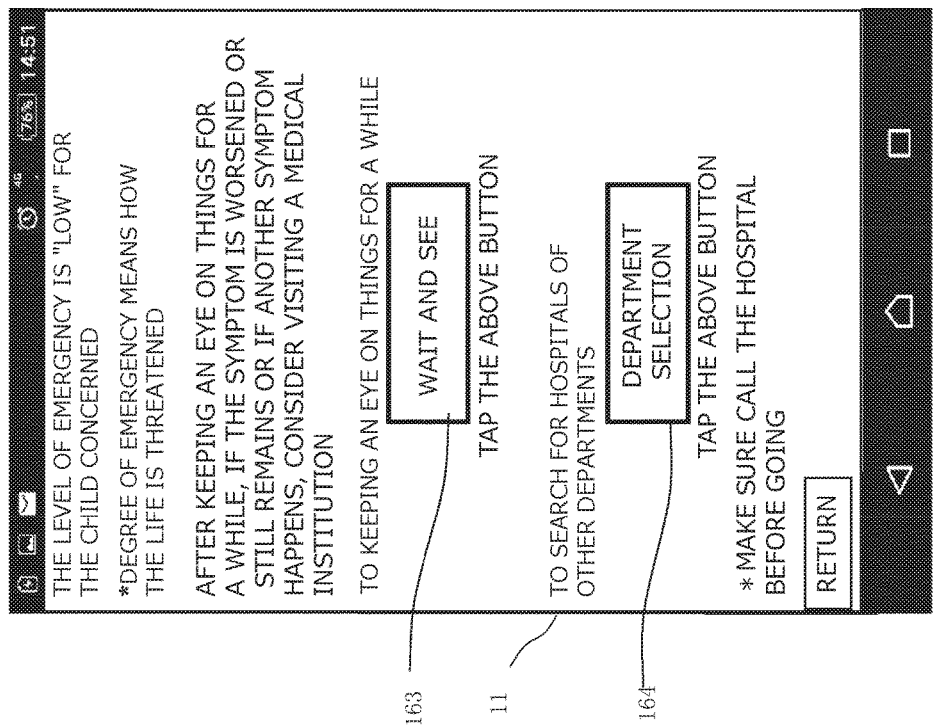
FIG. 11C shows the screen of the result corresponding to the determined emergency degree when the emergency degree is at a low level.

FIGS. 11A to 11C show the screens of the result in accordance with the determined emergency degree. FIG. 11A shows a high emergency level, FIG. 11B shows a medium emergency level, and FIG. 11C shows a low emergency level. FIG. 11A displays a "call 119" (119 is the telephone number for ambulance in Japan)" button 161 (fire-department button 161) that is the number of the emergency calling phone 32 associated beforehand (see FIG. 1) as well as a "#7119" button 162 that is the emergency consultation phone 33 associated beforehand (see FIG. 1) on the screen. The functions of these buttons 161 and 162 are described later. These buttons 161 and 162 can be represented in various modes.

In FIG. 11B, the screen displays the "#7119" button 162 and a "hospital search" button 143 (the same as in FIG. 9C) to search for nearby medical institutions of a specific department, "pediatrics" in this case. The function of the "hospital search" button 143 is described later. In FIG. 11C, the screen displays a "wait-and-see" button 163 and a "department selection" button 164. These buttons on the screen can implement their functions as described later when the user taps these buttons.

Figure 12:
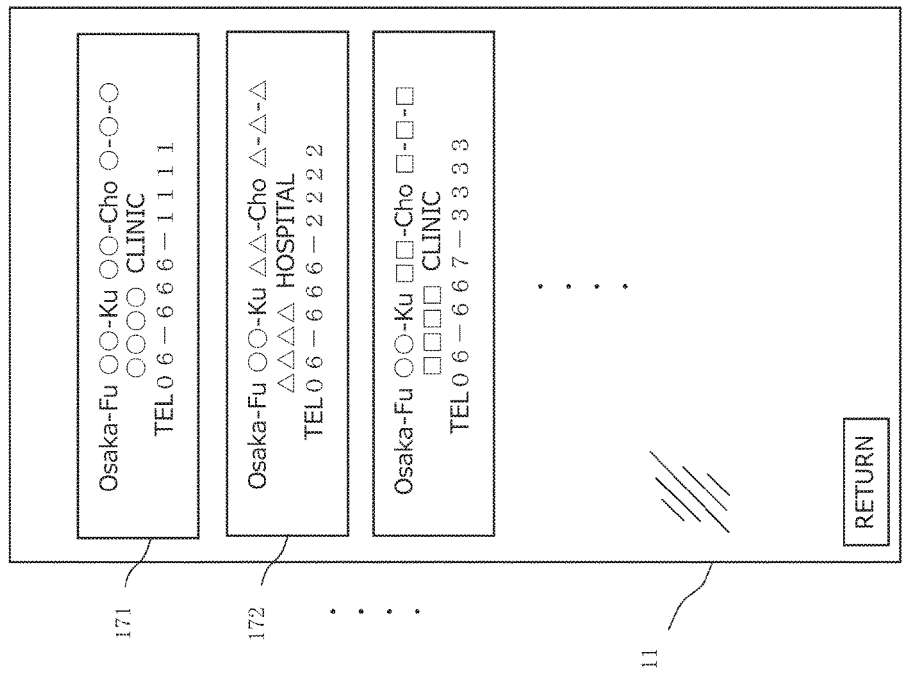
FIG. 12 shows an example of the screen showing the result when the user presses a "hospital search" button.
Figure 13A:
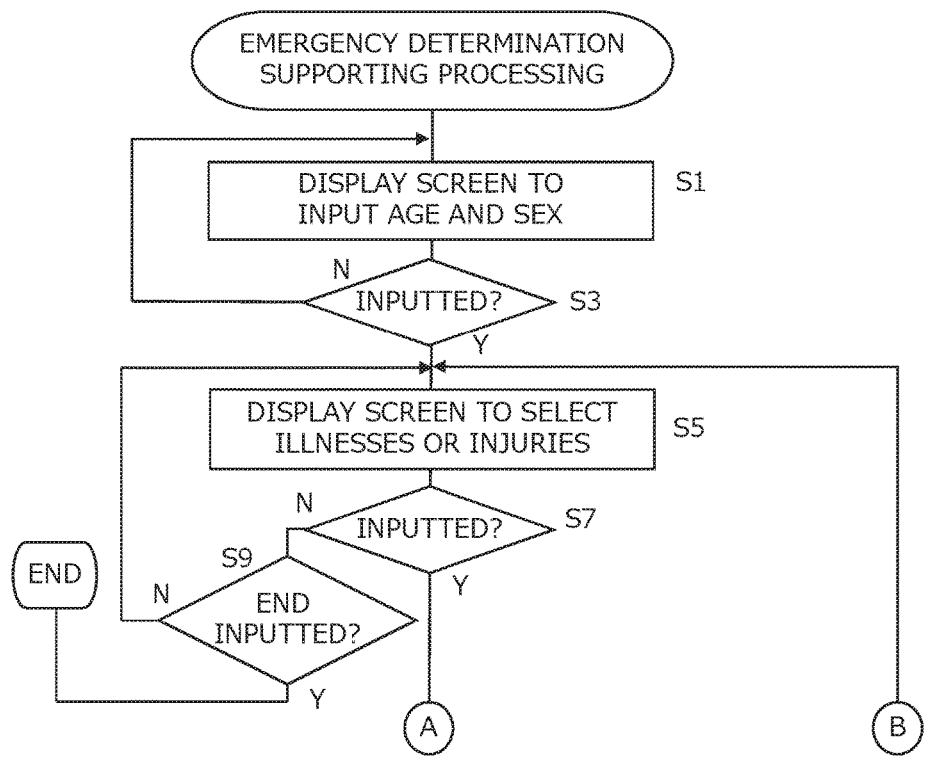
FIG. 13A is a flowchart to explain the procedure of the emergency support application downloaded in the storage unit of the terminal.
Figure 13B:
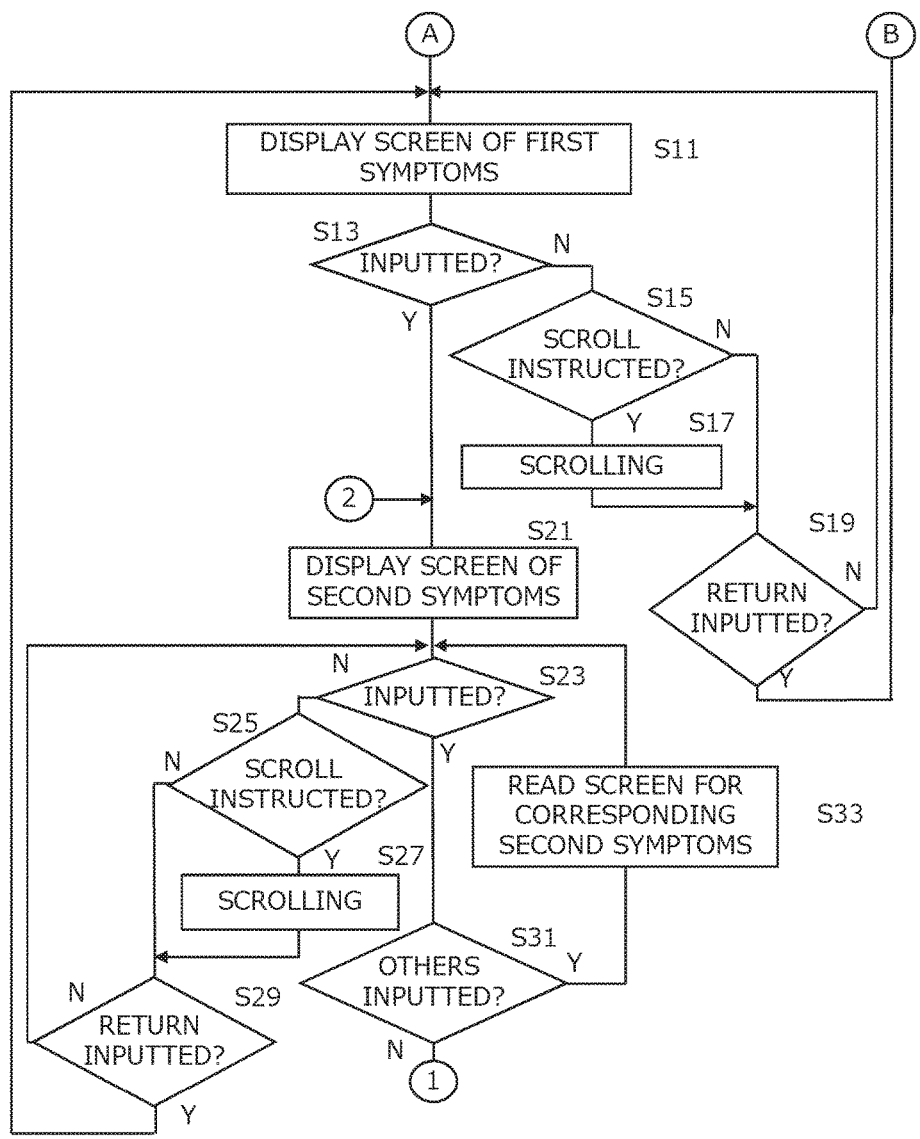
FIG. 13B is a flowchart to explain the procedure of the emergency support application downloaded in the storage unit of the terminal.
Figure 14A:
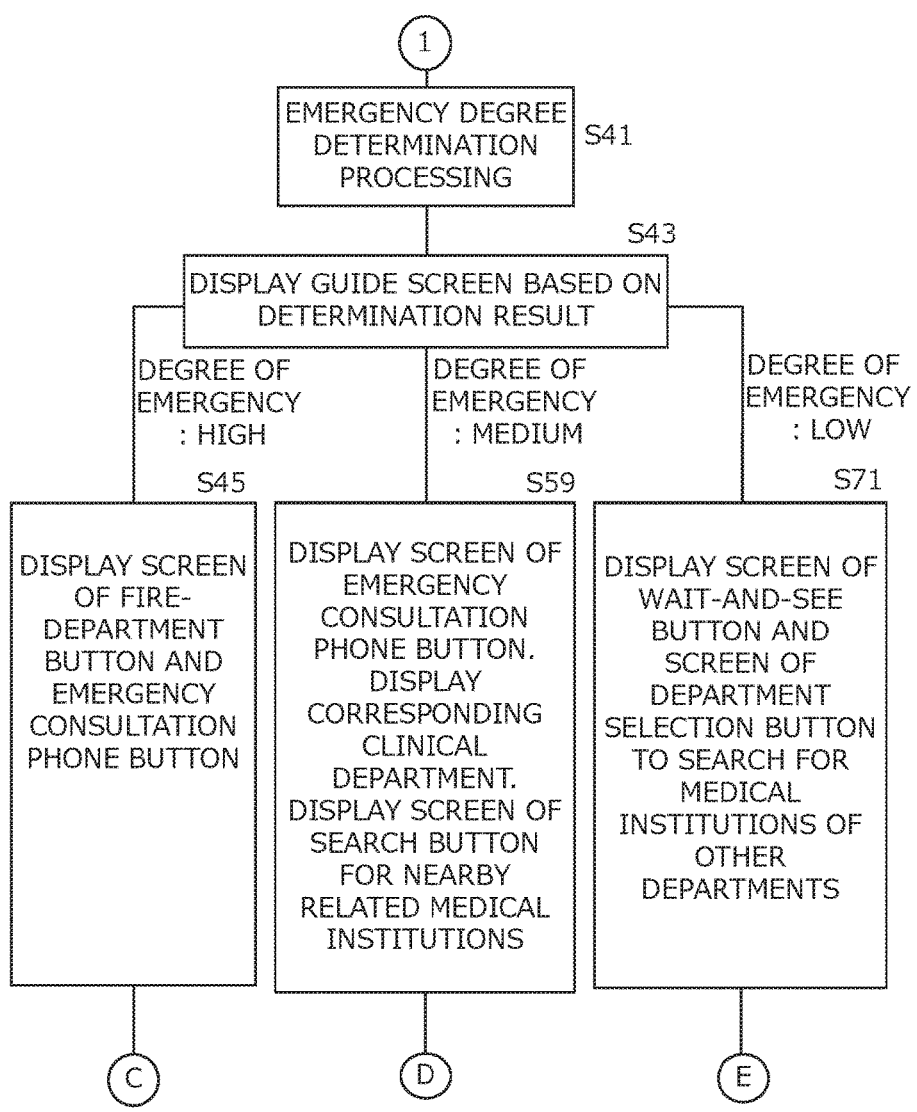
FIG. 14A is a flowchart to explain the procedure of the emergency support application downloaded in the storage unit of the terminal.
Figure 14B:
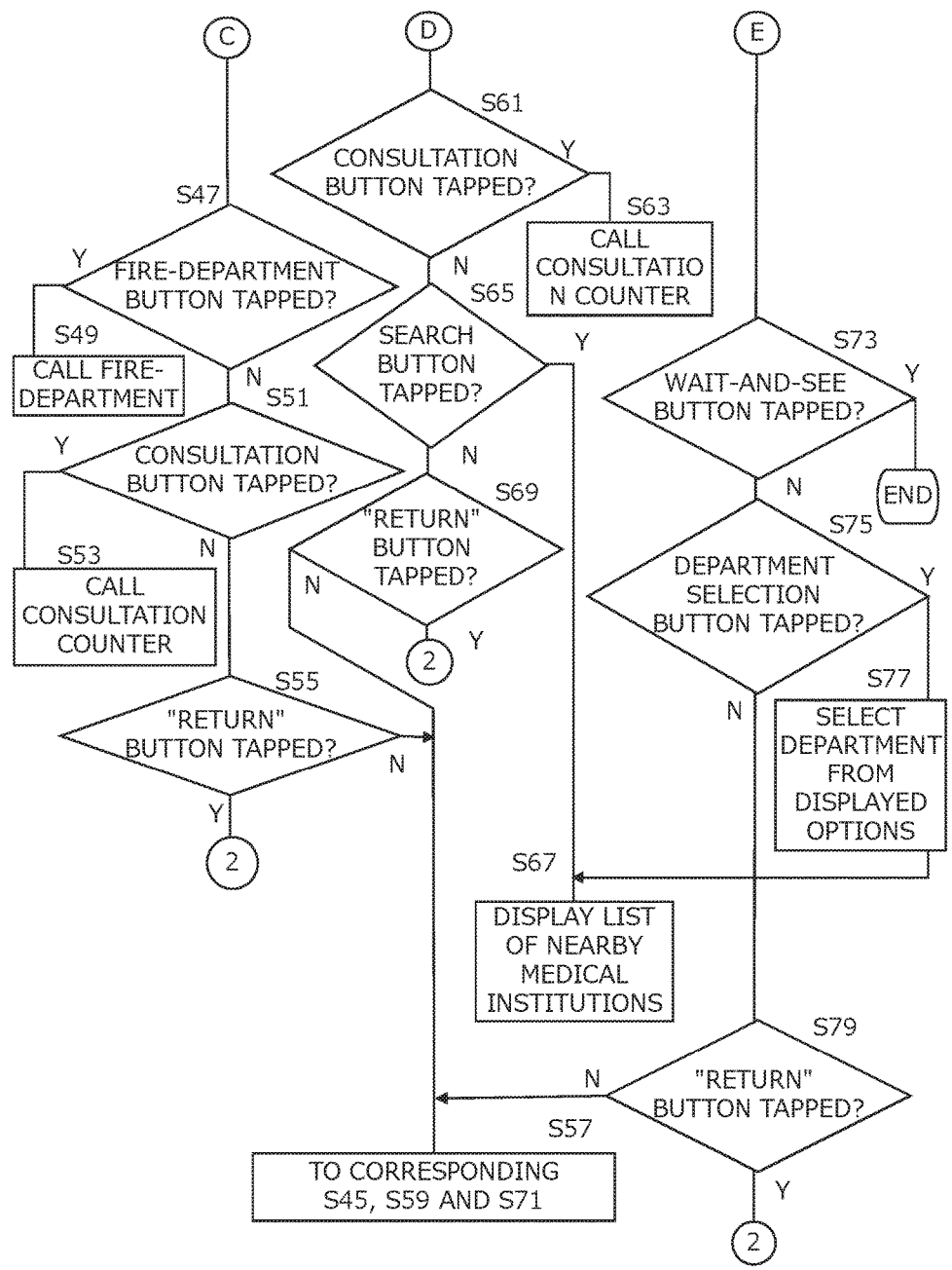
FIG. 14B is a flowchart to explain the procedure of the emergency support application downloaded in the storage unit of the terminal.

FIG. 12 shows an example of the screen showing the result when the user presses the "hospital search" button 143, displaying a list of information on the address, the name and the contact number of each of the searched medical institutions.

Referring to FIG. 3, the input reception unit 102 receives various types of input through the touch panel 12. The emergency determination unit 103 determines the emergency degree of the emergency transportation based on the symptoms that are selected and input as shown in FIG. 6B to FIG. 10C. The image display processing unit 101 reflects the determination result of the emergency degree in any one of the selection screens of FIG. 11A, FIG. 11B and FIG. 11C, for example.

The data communication/processing unit 104 controls all of the communication via the net communication unit 14 and the network 5, and the communication is performed with the management server 2 and other information devices. The data communication/processing unit 104 transmits the history of operations for each emergency case using the emergency support application to the management server 2 so that the management server stores it as log information.

When the user taps the button 161, 162 on the screen of FIG. 11A, 11B, the telephone network control unit (network control unit) 105 allows calling and talking with the emergency calling phone 32 or the emergency consultation phone 33 via the calling unit 15.

When the user taps the "hospital search" button 143 on the screen of FIG. 9C or FIG. 11B, the search unit 106 searches for nearby medical institutions and displays the search result on the display as in FIG. 12. More specifically when the user taps the "hospital search" button 143, the search unit 106 acquires positional information of the terminal 1 from the positioning device 13, checks the positional information for matching with information on medical institutions containing their positional information stored in the management server 2 (see FIG. 4) described later, and extracts a plurality of the medical institutions near the positional information of the terminal 1 or such medical institutions in the order of proximity, for example, in a predetermined area. Then the search unit displays a list of these medical institutions (FIG. 12). When the number of medical institutions for searching is large or the search area is wide, the management server 2 may execute such processing of the search unit 106 with consideration for the processing load of the terminal 1.

The time keeping unit 107 outputs date and time information. When the emergency support application activates or when the user presses the button 161, 162, for example, the input reception unit 102 temporarily loads such date and time information to be associated with the history of the operations. Positional information of the positioning device 13 also is loaded similarly. The positional information and the date and time information may be used as attribute information for the emergency case as needed.

The questionnaire processing unit 108 executes questionnaire processing that is a part of the emergency support application. More specifically the questionnaire processing unit 108 performs the following processing in the present embodiment: (1) in the case where the user did not call the emergency calling phone using the emergency support application (since it was not determined as high-emergency case, the user did not press the fire-department button 161), asking the user to cooperate in the questionnaire later; (2) keeping the time elapsed since the ending of the emergency support application; (3) when the user agreed to answer the questionnaire, determining the elapsed time as the questionnaire starting condition; (4) conducting the questionnaire; and (5) transmitting the result of questionnaire together with the attribute information on the person concerned and information on the input symptoms to the management server 2. This questionnaire processing is to ask a person who did not press the fire-department button 161 with the emergency support application (did not request an ambulance) at the end about whether they visited a medical institution after that or not, and to collect their history of medical care, for example.

Figure 4:
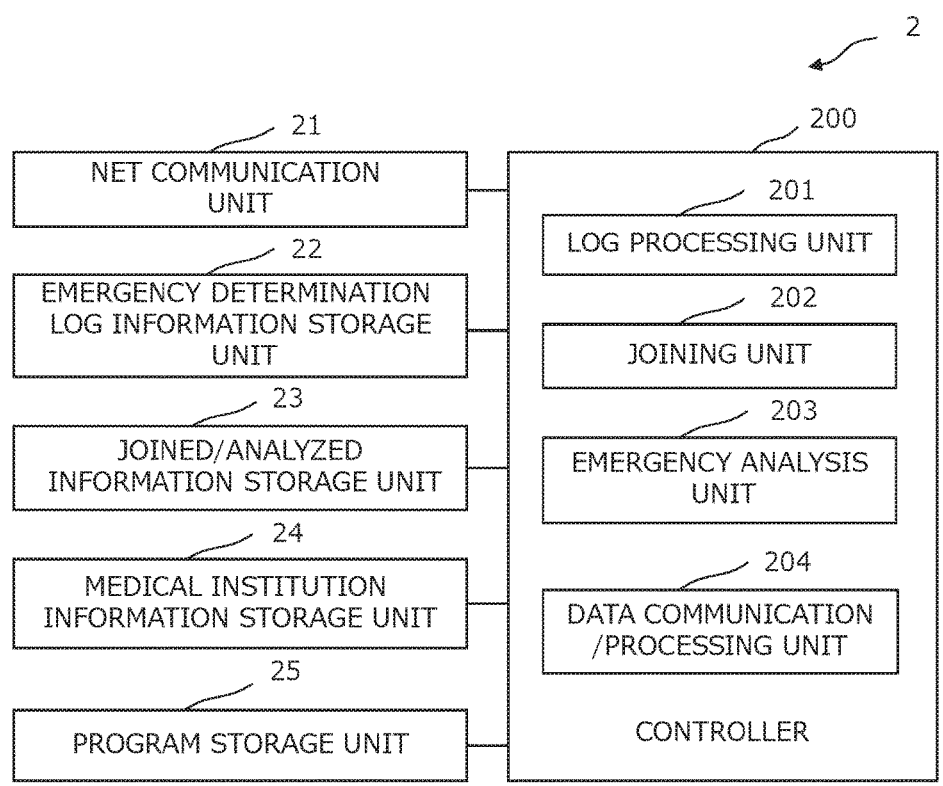
FIG. 4 shows the structure of a management server.

FIG. 4 shows the structure of the management server 2. The management server 2 functions as the first server, and includes a controller 200 made up of a computer and a net communication unit 21 connected to the controller 200 to exchange information with the terminal 1, the fire department server 3 and the medical institution server 4. The management server 2 has a function as a database. To this end, the management server includes an emergency determination log information storage unit 22, a joined/analyzed information storage unit 23, a medical institution information storage unit 24, and a program storage unit 25 that stores programs to execute various types of processing.

The emergency determination log information storage unit 22 acquires information on the input history when the user uses the emergency support application with the terminal 1 and stores such information to configure a database as log information. The emergency determination log information storage unit 22 also collects the acquired result of the questionnaire, that is, the history of consultation, medical care or the like of a person who was not determined at the end as high-level of emergency by the emergency support application, and so did not press the fire-department button 161, and configures a database as log information that includes the attribute information of the person concerned and the input information on the symptoms. The joined/analyzed information storage unit 23 stores the acquired log information, information on pre-hospital activity from the fire department server 3 and information on the progress after transportation from the medical institution server 4 that are joined and their analysis information, for example.

The medical institution information storage unit 24 stores information on the medical institutions (designated emergency hospitals) that has been registered to accept emergency patients in the area covered with the emergency support application, i.e., in the area at least including the area under the responsibility of the firefighting headquarter. To be used by injured or ill persons, such information on the medical institutions contains the name, the address, and the contact number, e.g., the telephone number of each medical institution. Considering the case of searching for and designating a hospital using the "hospital search" button 143, such information on the medical institutions also includes positional information registered in the same format as that of the positioning device 13 using latitude and longitude. This allows the distance between the positional information of the terminal 1 and the positional information of each of the registered medical institutions to be calculated during hospital searching, whereby the terminal 1 can extract nearby medical institutions. Based on the positional information, the medical institutions can be sorted in the order of proximity. When this emergency support application covers a wide area, typically covers a country as described later, each of the headquarter of the fire departments may manage the information on the medical institutions in their responsible area.

Through the execution of a program, the controller 200 functions as a log processing unit 201, a joining unit 202, an emergency analysis unit 203 and a data communication/processing unit 204. The log processing unit 201 sequentially stores the information on operation history for each emergency case transmitted from the terminal 1 in the emergency determination log information storage unit 22.

The joining unit 202 joins the log information in the emergency determination log information storage unit 22, the pre-hospital activity information from the fire department server 3 and the post-transportation progress information from the medical institution server 4. Joining of the information is performed by checking the attribute information on the injured or ill person against each other. The attribute information includes the age and the sex of the person that is input from the terminal 1 and at least one of the date and time information and the positional information as needed, and preferably includes both of them. Note here that the pre-hospital activity information from the fire department server 3 and the post-transportation progress information from the medical institution server 4 include the name of the injured or ill person in addition to the age, the sex, and the address of the person, the dispatched site of the firefighters, the time of the dispatch, and the time to transport the person to the medical institution. However, from the viewpoint of personal information protection, the emergency support application using the terminal 1 does not request the user to input their name. Therefore the information is joined based on the information other than the name.

Then the joining unit 202 checks the attribute information in the log information in the emergency determination log information storage unit 22 against the information on the injured or ill person in the pre-hospital activity information from the fire department server 3 and in the post-transportation progress information from the medical institution server 4 to join the information of each emergency case. Note here that the date and time information and the positional information may not be completely the same between the attribute information input from the terminal 1 and the pre-hospital activity information or the post-transportation progress information. Therefore agreement or not of such information preferably is determined by giving a certain degree of allowable width to the information. For the positional information, the joining unit can join the information based on substitution information that associates beforehand the positioning information (latitude and longitude) and the location information (e.g., the name of town, the block number and the like in accordance with the rules of address indication), for example. The joining unit 202 further joins the information on the person who inputted their symptoms with the emergency support application and became a target of the questionnaire. That is, the joining unit collects the symptoms that the person inputted with the application and the history of consultation at a medical institution where the person visited later (including a later date), e.g., the name of the medical institution and the details of the medical care from the questionnaire, and joins them with the attribute information of the person concerned and the input information on the symptoms to configure the information as an emergency case.

The emergency analysis unit 203 obtains statistical data of the relationship among the selected symptoms, the treatment and the details of the medical care for each of the joined emergency cases. This is obtained based on the log information from the terminal 1, the pre-hospital activity information from the fire department server 3 and the post-transportation progress information from the medical institution server 4 as well as the symptoms obtained from the history of input operations and the history of consultation and medical care after the case that are obtained from the questionnaire. Then the emergency analysis unit evaluates the appropriateness of the symptoms and the emergency degree for each emergency case based on the medical algorithm (such as CTAS or JTAS as stated above). For instance, if the analysis result of the statistical data shows that many emergency cases for a symptom have an emergency degree different from the currently set relationship between the symptom and the emergency degree (high, medium, or low), for example, such a relationship between the symptom and the emergency degree is desirably changed. The emergency analysis unit 203 executes the analysis processing when a predetermined condition of analysis timing is achieved. For instance, the condition of analysis timing is when a predetermined period of time, e.g., 1 or 2 years, has passed, or when the number of emergency cases increases to a predetermined number. Alternatively this may be the timing when reevaluation is required because of large statistical dispersion.

The data communication/processing unit 204 controls the exchange of data between the terminal 1, the fire department server 3 and the medical institution server 4.

Figure 5A:
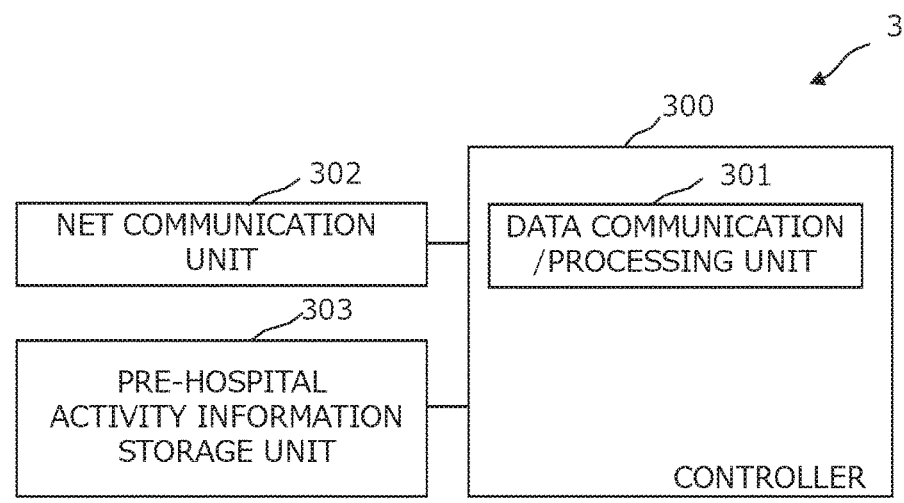
FIG. 5A shows the configuration of a fire department server.
Figure 5B:
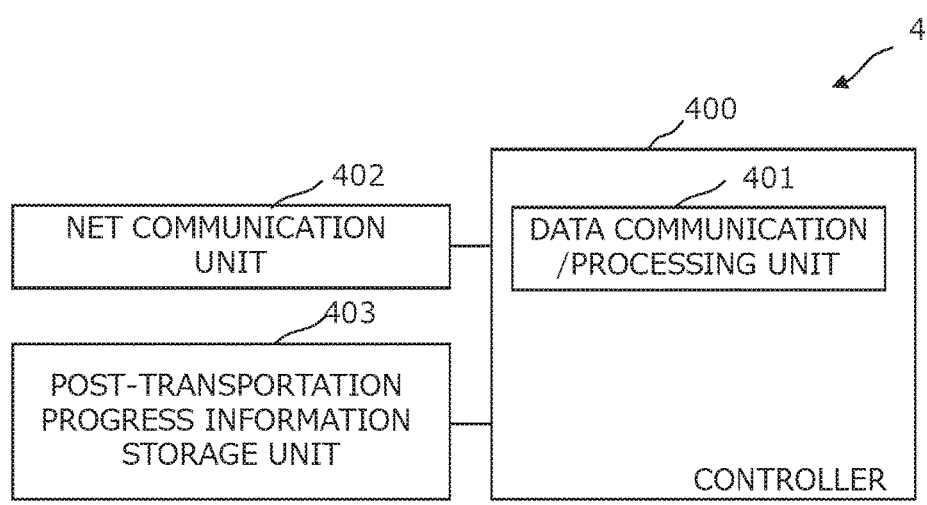
FIG. 5B shows the configuration of a medical institution server.

FIG. 5A shows the configuration of the fire department server 3, and FIG. 5B shows the configuration of the medical institution server 4. In FIG. 5A, the fire department server 3 functions as a data server, and includes a controller 300 having a data communication/processing unit 301, and a net communication unit 302 and a pre-hospital activity information storage unit 303 that are connected to the controller 300. The net communication unit 302 communicates with the management server 2 and the firefighter terminal 31 via the network 5. The data communication/processing unit 301 writes pre-hospital activity information input from the firefighter terminal 31 via the net communication unit 302 for each emergency case in the pre-hospital activity information storage unit 303. To evaluate and analysis the information, the data communication/processing unit 301 transmits the pre-hospital activity information in the pre-hospital activity information storage unit 303 to the management server 2.

In FIG. 5B, the medical institution server 4 functions as a data server, and includes a controller 400 having a data communication/processing unit 401, and a net communication unit 402 and a post-transportation progress information storage unit 403 that are connected to the controller 400. The net communication unit 402 communicates with the management server 2 and the medical-institution terminal 41 via the network 5. The data communication/processing unit 401 writes post-transportation progress information input from the medical-institution terminal 41 via the net communication unit 402 for each emergency case in the post-transportation progress information storage unit 403. To evaluate and analysis the information, the data communication/processing unit 401 transmits the post-transportation progress information in the post-transportation progress information storage unit 403 to the management server 2.

FIGS. 13A to 14B are flowcharts to explain the procedure of the emergency support application downloaded in the storage unit 110 of the terminal 1. When the user presses the icon 10b corresponding to the emergency support application to activate the emergency support application, the terminal displays a reception screen (see FIG. 6A) for inputting the age and the sex (Step S1).

When the user inputs the age and the sex and taps the next button 113 (Yes at Step S3), the terminal displays an injury/illness selection screen (See FIG. 6B) having an "illness" button 114 and an "injury/foreign substances" button 115 (Step S5). When the terminal does not receive any selection or input (No at Step S7), then determination is made whether the user pressed an end button 116 or not (Step S9). When the user pressed the button, the emergency support application ends.

When the user taps one of the "illness" button 114 and the "injury/foreign substances" button 115 (Yes at Step S7), the terminal displays a list of symptoms (FIG. 7A or FIG. 7B) for the types of the illnesses or injuries that is tapped as a screen of first symptoms (Step S11). Next determination is made whether any one of the symptoms is selected and input or not (Step S13). When the screen does not display all of the symptoms, the user may swipe the screen up and down (Step S15) for scrolling of the screen (Step S17). When the user taps the return button (Step S19), the screen returns to the state for selection between illnesses and injuries at Step S5.

When the user selects any one of the symptoms at the screen of first symptoms, the terminal displays a list of second symptoms that are at a low hierarchical level of the selected symptom as a screen of second symptoms (Step S21). For instance, when the user selects "fever" at the screen of first symptoms, the terminal then displays the screen of FIG. 8A that is a list of symptoms at a low hierarchical level of "fever" as a screen of second symptoms. When the user selects "convulsion" at the screen of first symptoms, the terminal displays the screen of FIG. 9A that is a list of symptoms at a low hierarchical level of "convulsion" as a screen of second symptoms. When the user selects "trauma of head or neck" at the screen of first symptoms, the terminal displays the screen of FIG. 10A that is a list of symptoms at a low hierarchical level of "trauma of head or neck" as a screen of second symptoms.

For the screen of second symptoms, determination is made whether the user selected and inputted any one of the symptoms or not (Step S23). When the user swipes the screen (Step S25), the screen is scrolled (Step S27). When "fever" is selected, for example, the screen will be scrolled from FIG. 8A to FIG. 8C. When "convulsion" is selected, for example, the screen will be scrolled between FIG. 9A and FIG. 9C. When "trauma of head or neck" is selected, for example, the screen will be scrolled between FIG. 10A and FIG. 10C.

When the user taps the return button, the procedure returns to Step S11. When it is determined at Step S23 that the user inputted, determination is made whether this is inputting for others or not (Step S31). When this is inputting for others, the screen of second symptoms corresponding to the selected button for others is read (Step S33), and the procedure shifts to Step S23. The button for others includes the button 134, 135 or 136 in FIGS. 8A to 8C, for example. These buttons show the symptoms that are other than the symptoms for "fever" and can be factors of severe cases. This enables jumping to other symptoms so as to give the user a wider range of options and allow the user to extract a more appropriate symptom.

When it is determined at Step S23 that the user selected and inputted any one of the symptoms and did not input for others, then it is determined that the operation to select symptoms by the injured or ill person ends. Then emergency determination processing is performed, where the emergency degree is set beforehand for the attribute information and each of the symptoms (Step S41). In the present embodiment, the emergency degree is displayed for each symptom so that the user can identify it. For instance, any one of the red mark, the yellow mark and the green mark is displayed at the left edge of the symptom.

When the determination processing ends, the terminal displays a guide screen corresponding to the result of determination (Step S43). More specifically when the emergency degree is at a high level, the screen displays the fire department button (the "call 119" button 161) and the emergency consultation phone button (the "#7119" button 162) (Step S45, see FIG. 11A). When the emergency degree is at a medium level, the screen displays the emergency consultation phone button 162, the name of the corresponding clinical department and the "hospital search" button 143 to search for nearby relating medical institutions (Step S59, see FIG. 11B). When the emergency degree is at a low level, the screen displays the "wait-and-see" button 163 and the "department selection" button 164 to search for medical institutions of other clinical departments (Step S71, see FIG. 11C).

Next, in the case of high-level emergency, determination is made whether the "call 119" button 161 is tapped or not (Step S47). When it is tapped, the terminal controls the calling function to start the calling the emergency calling phone 32 (Step S49). When it is not tapped at Step S47, determination is made whether the "#7119" button 162 is tapped or not (Step S51). When it is tapped, the terminal controls the calling function to start the calling the emergency consultation phone 33 (Step S53). When it is not tapped at Step S51, determination is made whether the return button is tapped or not (Step S55). When it is tapped, the procedure returns to Step S21. When it is not tapped, the procedure returns to Step S45 (Step S57).

In the case of medium-level emergency, determination is made whether the "#7119" button 162 is tapped or not (Step S61). When it is tapped, the terminal controls the calling function to start the calling the emergency consultation phone 33 (Step S63). When it is not tapped at Step S61, determination is made whether the "hospital search" button 143 is tapped or not (Step S65). When it is tapped, nearby medical institutions are searched as stated above, and the terminal displays a list of the searched medical institutions on the screen (Step S67, see FIG. 12). When the "hospital search" button 143 is not tapped, determination is made whether the return button is tapped or not (Step S69). When it is tapped, the procedure returns to Step S21. When it is not tapped, the procedure returns to Step S59 (Step S57).

In the case of low-level emergency, determination is made whether the "wait-and-see" button 163 is tapped or not (Step S73). When it is tapped, the emergency support application ends. When the "wait-and-see" button 163 is not tapped, determination is made whether the "department selection" button 164 is tapped or not (Step S75). When it is tapped, nearby medical institutions of the clinical department selected from the displayed departments for selection (Step S77) are searched, and the terminal displays a list of the searched medical institutions on the screen (Step S67, see FIG. 12). When the "department selection" button 164 is not tapped, determination is made whether the return button is tapped or not (Step S79). When it is tapped, the procedure returns to Step S21. When it is not tapped, the procedure returns to Step S71 (Step S57).

Figure 15:
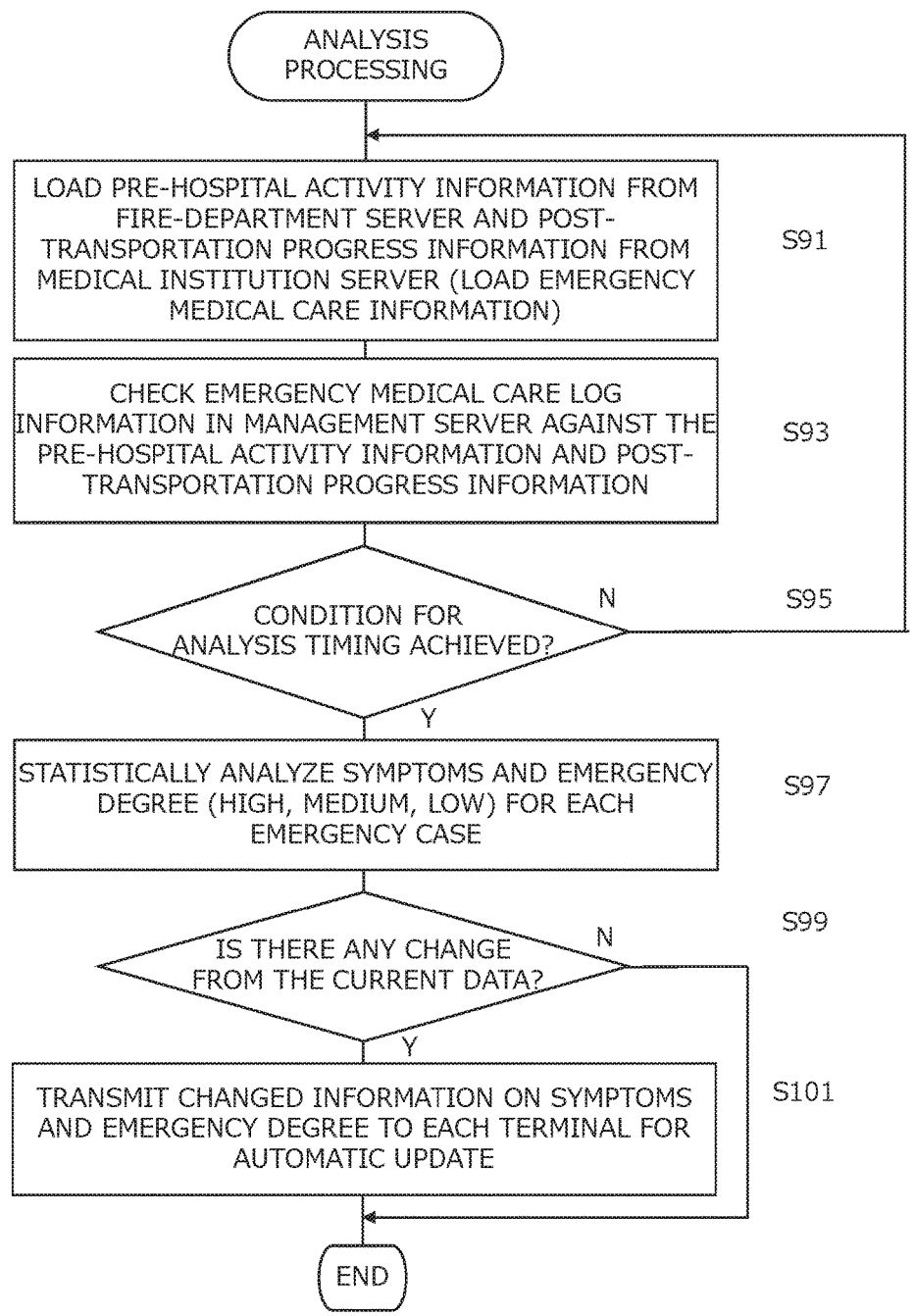
FIG. 15 is a flowchart executed by the management server to analysis the relationship of the symptoms and the emergency degree.

FIG. 15 is a flowchart executed by the management server 2 to evaluate and analysis the relationship of the symptoms and the emergency degree based on the cases having high level of emergency and requesting an ambulance. Firstly the management server loads the pre-hospital activity information and the post-transportation progress information from the fire department server 3 and the medical institution server 4, respectively (Step S91). Next, the management server 2 checks the log information on emergency care in the management server against the pre-hospital activity information and the post-transportation progress information by a method as described above for each emergency case (Step S93). When the checking ends, the management server determines whether the condition for analysis timing as stated above is achieved or not (Step S95). When the condition for analysis timing is not achieved, the procedure returns to Step S91. When the condition for analysis timing is achieved, the management server statistically analyzes the symptoms and the emergency degree for the emergency case having the information that can be joined successfully (Step S97). At this step, the management server compares the result of the statistical analysis this time with the currently set relationship between the symptoms and levels of the emergency degree. Then the management server determines whether there is a difference in relationship between them, or when there is a difference, determines about the ratio of the cases having such a difference, for example (Step S99). When the result of comparison shows that they agree completely or substantially completely, the management server ends this procedure. When the result shows that there is a difference partly, the management server revises the algorithm to determine the emergency degree so that the part having a difference can have a new relationship between the symptoms and the levels of emergency degree so as to update the emergency support application (upgrade the version, for example) (Step S101). When the level of emergency degree set for a symptom is changed, the new relationship may include the case where a symptom is newly added at the level of emergency degree or a symptom is removed from the level, for example.

Such analysis processing is similarly applied to the result of emergency cases that are obtained from the questionnaire processing. For the case having low-level of emergency and not requesting an ambulance, the user is asked to answer the questionnaire within a certain period of time after the user used the emergency support application, for example, about whether the user visited a medical institutions for the case or not. The users may voluntarily answer the questionnaire or be obligated to answer the questionnaire. For the case of visiting a medical institution, the questionnaire may include appropriate questions to ask the user about the result of the visiting of a medical institution including whether they were hospitalized for treatment or not, for example. When the medical institution is known, detailed and correct information on the medical care can be acquired from the medical institution. The management server then statistically analyzes the data based on whether the user visited the medical institution or not, the result of the consultation at the medical institution, and the result of determination for emergency with the emergency support application to verify the appropriateness of the emergency degree determined by comparing the result with the currently set relationship between the symptoms and the levels of emergency degree. A result of the verification is handled similarly to the cases of having high-level of emergency and requesting an ambulance, whereby the algorithm to determine the emergency degree is revised as needed so as to update the emergency support application to be more reliable.

Preferably the data communication/processing unit 204 updates the terminal 1 with the updated emergency support application through automatically distribution every time when the application is changed or on a regular basis. Alternatively information on updating is distributed to the terminal 1, and the user may operate the terminal for updating. The distribution maybe performed directly, or may be via a site selling applications over the network 5.

Figure 16:
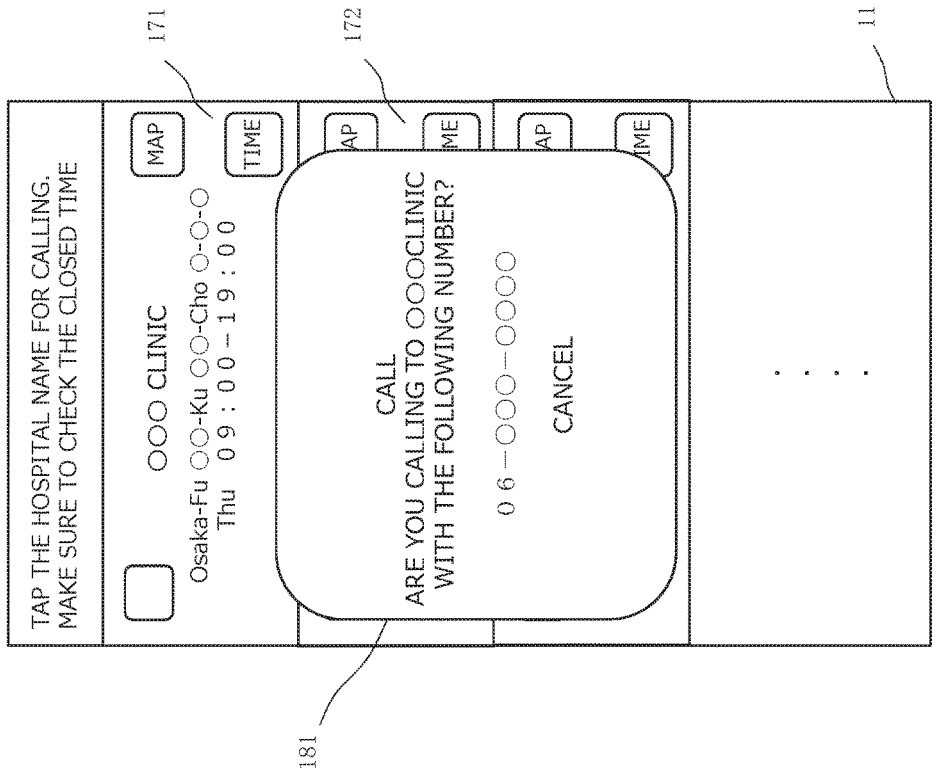
FIG. 16 shows one example of the final screen when the user does not press the fire-department button.

Referring next to FIGS. 16 to 22, the following describes the questionnaire processing. FIG. 16 shows one example of the final screen of the emergency support application that shows a result of hospital search (corresponding to FIG. 12). This drawing shows a screen for selection between tapping the name of a hospital for calling and tapping the cancel button 181, and the user selects the cancel to end the emergency determination processing, in one example.

Figure 17:
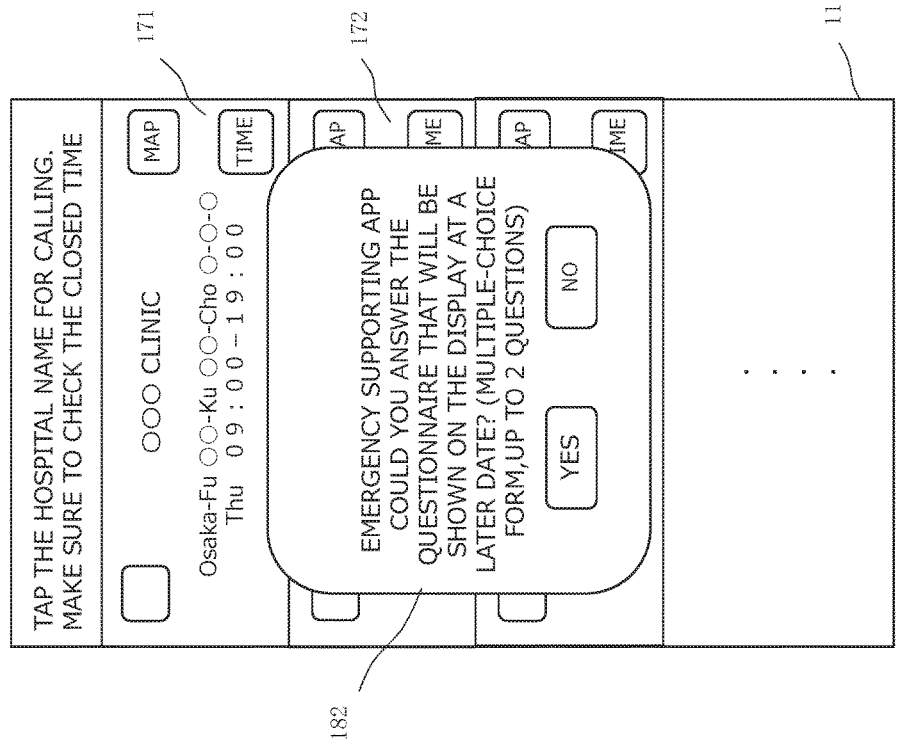
FIG. 17 shows one example of the screen to ask the user to cooperate in questionnaire.

FIG. 17 is one example of the screen that is displayed following the screen of FIG. 16. FIG. 17 shows the screen before ending when the case is not high in emergency and so an ambulance is not requested. The screen asks the user to cooperate in filling out the questionnaire after the case. The screen shows a sub-screen 182 that displays "Yes" and "No" buttons to answer about the cooperation in questionnaire.

Figure 18:
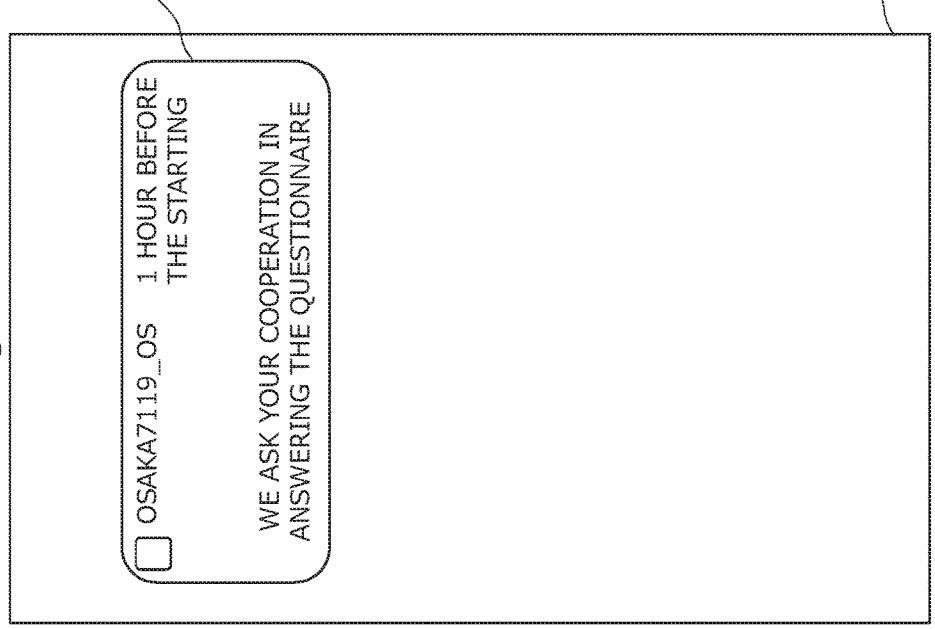
FIG. 18 shows one example of the notice screen before the questionnaire.

FIG. 18 shows a notice screen 183 that is displayed a predetermined period of time, e.g., one hour before the starting of the questionnaire processing when the user presses the "Yes" button in FIG. 17.

FIG. 19 shows a Q1 screen 191 that is displayed at the starting of the questionnaire processing when the user presses the "Yes" button in FIG. 17. The screen includes a plurality of questions, e.g., six questions as the question Q1. When the user taps (selects) the display position of each sentence of the question, the screen is switched.

FIG. 20 shows a Q2 screen 192 that is the screen following the selection of questions 1, 2, 4 and 6 in the Q1 screen 191 of FIG. 19. The questions in the Q2 screen 192 relate to the questions 1, 2, 4 and 6 in the Q1 screen 191 to collect more detailed history.

FIG. 21 shows a Q3 screen 193 that is the screen following the selection of questions 3 and 5 in the Q1 screen 191 of FIG. 19. The questions in the Q3 screen 193 relate to the questions 3 and 5 in the Q1 screen 191 to collect more detailed history.

Figure 22:
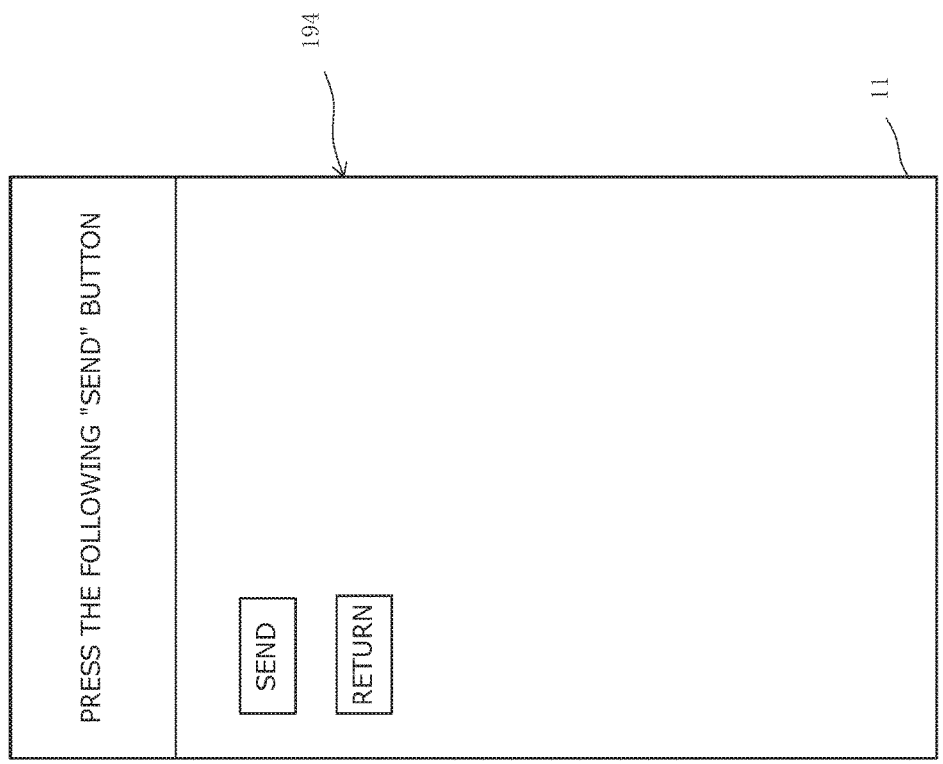
FIG. 22 shows one example of the screen to send the result of the questionnaire.

FIG. 22 shows a send screen 194 that is displayed after switching when the user taps (selects) the display position of each sentence in the questions Q2 and Q3. The send screen 194 displays a send button and a return button. When the user taps the send button, the answers for the questions Q1 to Q3 are sent to the management server 2. When the user taps the return button, the screen returns to the state of one of the questions Q2 and Q3 to allow the user to select the answers again.

Figure 23:
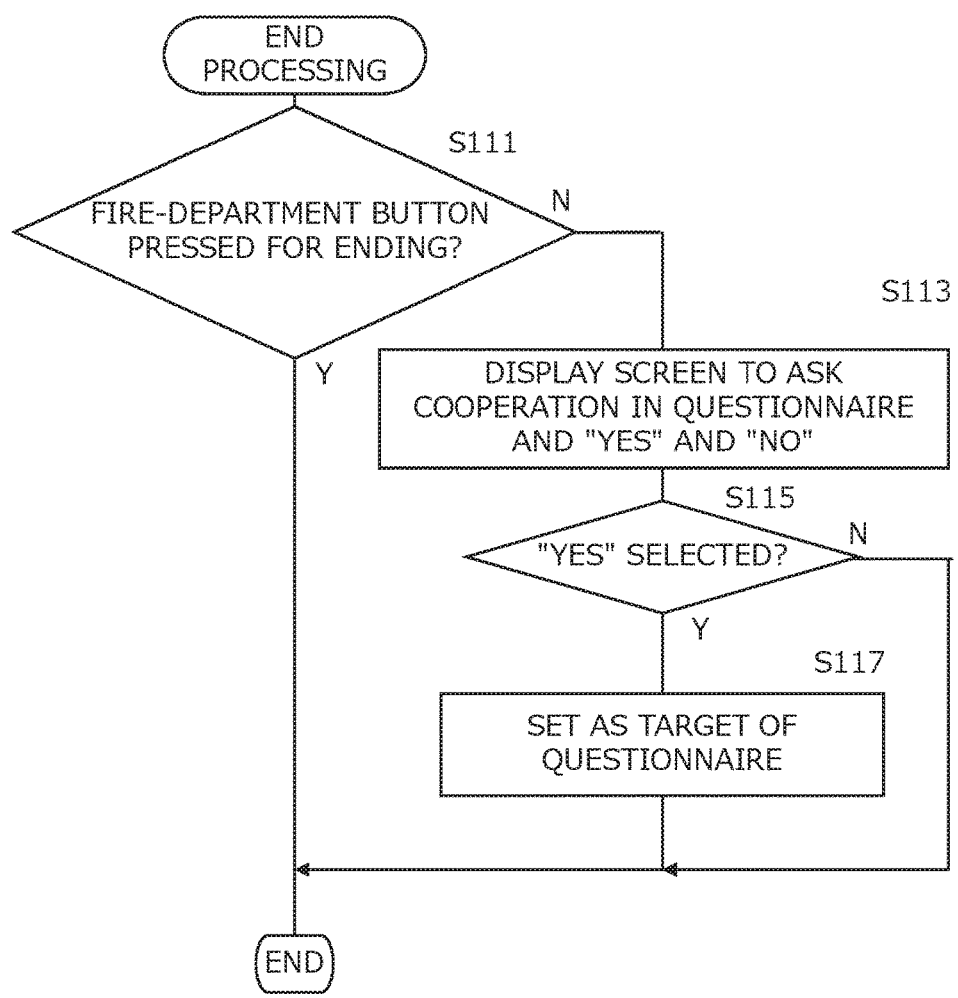
FIG. 23 is a flowchart executed by the terminal to end the emergency support application.
Figure 24:
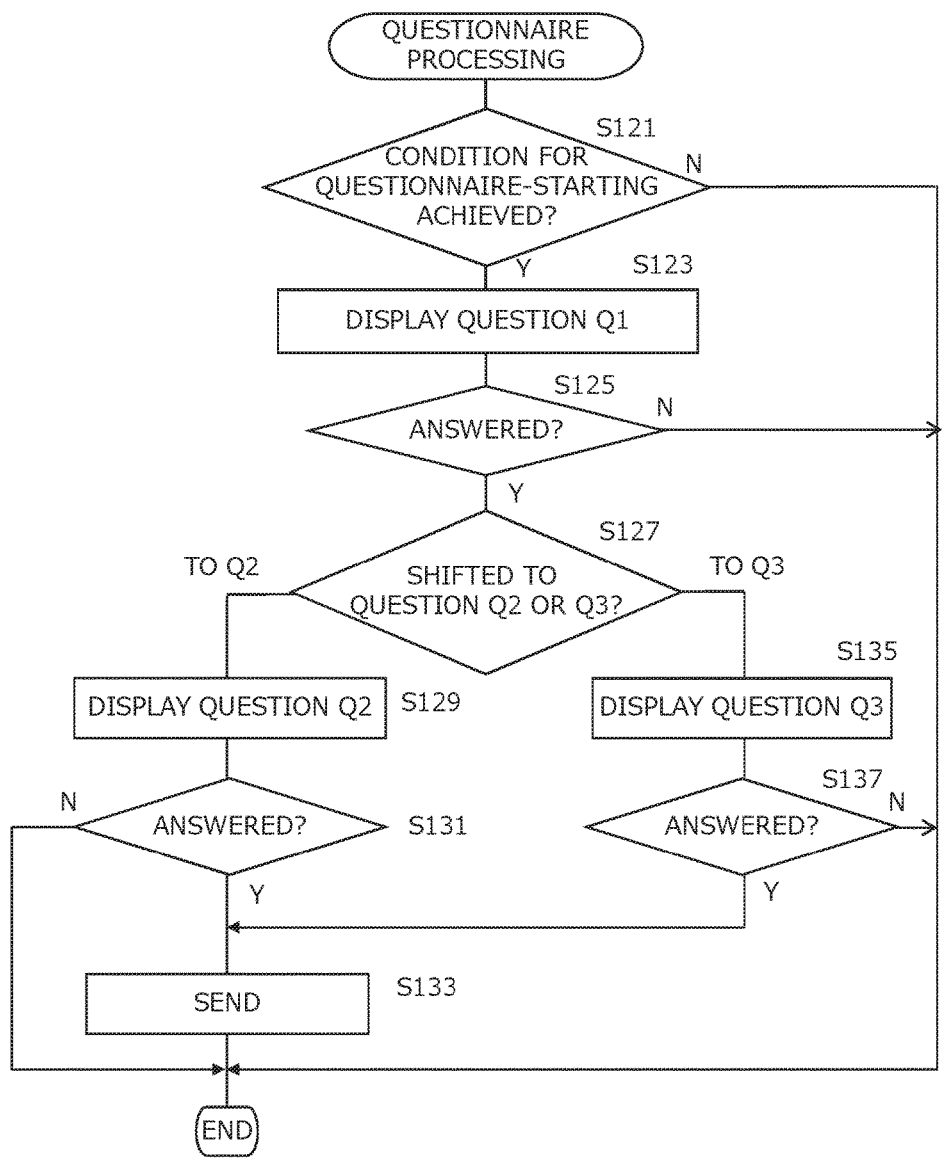
FIG. 24 is a flowchart showing one example of the questionnaire processing executed by the terminal.
Figure 25:
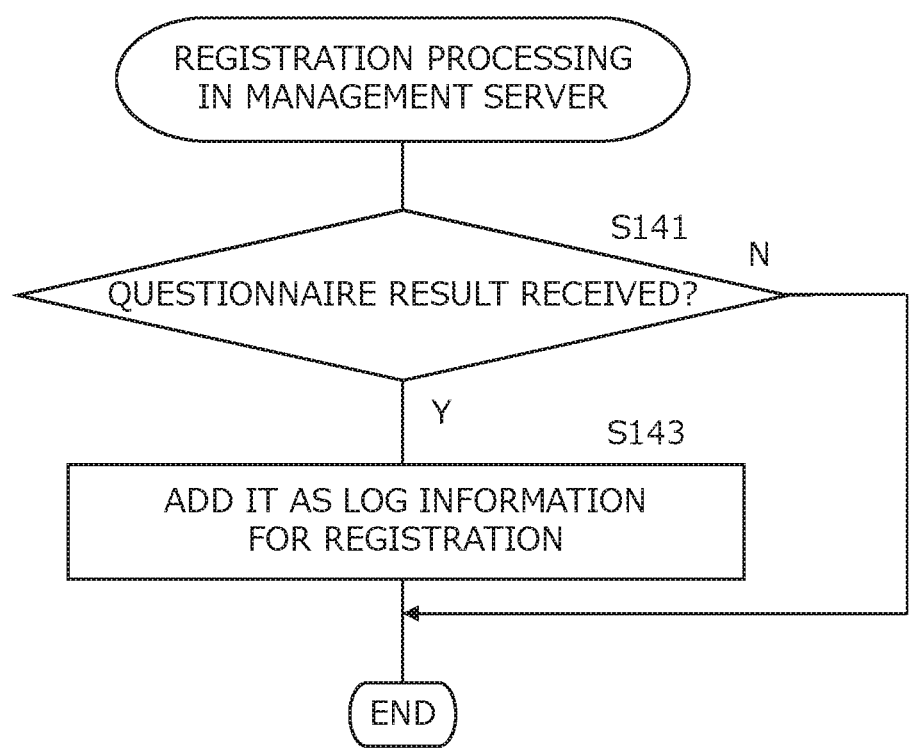
FIG. 25 is a flowchart executed by the management server to register the result of questionnaire.

Referring next to the flowcharts of FIGS. 23 to 25, the following describes the questionnaire processing. FIG. 23 shows the processing following the final processing (Yes at Steps S49, S53, S63, S67 and S73) of the flowchart for emergency determination processing shown in FIG. 14. In FIG. 23, determination is firstly made whether the user presses the fire-department button 161 in the emergency determination processing (meaning that the case is high in emergency) (Step S111). When the fire-department button 161 is pressed, it is determined that the case is at a high level in emergency. In this case, since the pre-hospital activity information and the post-transportation progress information can be obtained, the procedure ends.

When the user does not press the fire-department button 161, it is determined that case is not at a high level in emergency. In this case, since the pre-hospital activity information and the post-transportation progress information cannot be obtained, then a screen to ask for cooperation in questionnaire is displayed (Step S113). Next, when pressing of the "Yes" button is confirmed (Step S115), the user is set as a target of the questionnaire (Step S117). When pressing of the "No" button is confirmed (No at Step S115), the user is not set as a target of the questionnaire, and the procedure ends.

FIG. 24 is a flowchart showing the procedure of answering the questionnaire with the terminal 1. Firstly determination is made whether the condition for questionnaire-starting as stated above is achieved or not (Step S121). When the condition for questionnaire-starting is not achieved, the procedure goes to the end. When it is determined at the condition for questionnaire-starting is achieved, the screen displays the question Q1 (Step S123). When the user answers the question Q1 (Step S125), determination is made based on the answer to which one of the questions Q2 and Q3 the case corresponds (Step S127). When the case corresponds to the question Q2, the screen displays the question Q2 (Step S129). When the user answers the question Q2 (Step S131), the result is sent to the management server 2 (Step S133) and the procedure ends. When the case corresponds to the question Q3 at Step S127, the screen displays the question Q3 (Step S135). When the user answers the question Q3 (Step S137), the result of questionnaire is sent to the management server 2 together with the attribute information on the person concerned and information on the input symptoms (Step S133) and the procedure ends.

FIG. 25 is a flowchart showing the registration processing of the result of questionnaire by the management server 2. Firstly the management server determines whether the result of questionnaire is transmitted from any one of the terminals 1 or not (Step S141). When receiving the result of questionnaire, the management server adds and registers the received result of questionnaire as log information (Step S143). For instance, for registration, the result of questionnaire is joined with the already registered log information on the attribute information and the symptoms that are input with the emergency support application. The attribute information and the symptoms may be collectively sent to the management server during sending of the result of questionnaire.

In the present embodiment, the symptoms are selected on the tree-shaped and two hierarchical levels of selection screens, and any desired number of hierarchical levels may be set depending on the number of cases, for example.

The target medical institutions to be searched for with the "hospital search" button 143 are not limited to designated emergency hospitals, and may include all of the medical institutions.

In another mode, the attribute information to be used for checking may include information that can identify individuals, such as individual names. In another mode, information to authenticate individuals may be used.

In the present embodiment, the management server 2 to store the log information for emergency determination statistically evaluates and analyzes the relationship between symptoms and the level of emergency degree. In another mode, another device may perform such evaluation and analysis. In another mode, the management server 2 may be independent of the fire department server 3 or a typical medical institution server 4, for example, in software, but may share the hardware with these servers.

In the present embodiment, the terminal 1 loads the data on symptoms and the data on the screen to display the emergency degree, and the management server 2 stores information on medical institutions to be searched. The device to store the information can be set appropriately considering the capacity of the memory, the processing speed and other points.

In a mode configured to apply this emergency support application to a wider area, e.g., nationwide, the present system may be configured for the area where each fire-fighting headquarter is responsible for. Although the pre-hospital activity information and the post-transportation progress information are collected in the area where each fire-fighting headquarter is responsible for, the relationship between symptoms and the emergency degree has to be collected to be uniform throughout the nation. Therefore the data throughout the nation may be collected, and an integrated management server configured above the management server 2, for example, may analyze the data.

In the present embodiment, the terminal 1 mainly performs the questionnaire processing. Alternatively the management server 2 may perform this mainly. More specifically, the management server manages the condition for starting questionnaire and manages an interactive communication about the questionnaire and the answer thereof.

As described above, a program according to the present invention supports emergency determination with an information terminal equipped with a display and an operating unit. The program makes the information terminal function as: an injured/ill person information reception means configured to receive input of attribute information on an injured or ill person through the operating unit of the information terminal; a symptom selection means configured to display a plurality of symptoms on the display of the information terminal to allow a user to select any symptom from the plurality of symptoms through the operating unit; and an emergency determination means configured to determine the emergency degree corresponding to the attribute information and the selected symptom and notify the emergency degree to the user.

The present invention can inhibit non-urgent request for ambulance for proper dispatching of ambulance. This can contribute to shortening the arrival time of ambulance.

Preferably the attribute information includes age and sex. This information together with the selected symptom enables more correct determination of the emergency degree. The user can input such attribute information with the information terminal and is not required to input information that can identify the injured or ill person.

The plurality of symptoms has a plurality of hierarchical levels, and is configured to be a tree form to specify the symptom to be more subdivided according to the hierarchical levels. The symptom selection means allows the user to select any symptom at each hierarchical level from an upper level. The emergency determination means preferably determines the emergency degree based on the attribute information of the injured or ill person and at least the symptom selected at the lowest hierarchical level. With this configuration, since a plurality of symptoms is arranged to be a tree form (hierarchically), the user can easily find the corresponding symptoms. The emergency degree may be determined while considering the history of selection of symptoms together with the symptom selected at the lowest hierarchical level for more correct determination.

Preferably the highest hierarchical level specifies whether the symptom corresponds to injuries or illnesses. With this configuration, the symptom can be roughly classified into injuries and illnesses for the first selection, whereby the user can easily select the symptoms in the following procedure.

Preferably the information terminal includes a calling unit. When the emergency degree is determined as a high level, the information terminal then functions as an image display processing means configured to display an emergency calling button on the display. When the user presses the emergency calling button, the information terminal functions as a telephone network control means to make a call via the calling unit to an emergency call phone that is associated beforehand. With this configuration, when the emergency degree is determined as a high level, the information terminal displays the emergency calling button on the display, and when the user presses the emergency calling button, the information terminal can make a call via the calling unit to an emergency call phone (in Japan, 119) that is associated beforehand. In the case of the high level of emergency, the user can simply press the displayed button for emergency call. In this way, this can improve the convenience of the user.

Preferably when the emergency degree is determined as a level lower by one than the high level, the image display processing means displays an emergency consultation phone button on the display. When the user presses the emergency consultation phone button, the telephone network control means makes a call via the calling unit to an emergency consultation phone that is associated beforehand. In the case of the determination as a level lower by one than the high level of emergency, the user can simply press the displayed button for emergency consultation call. In this way, this can improve the convenience of the user. This button for emergency consultation phone may be displayed for the emergency degree at the high level as well. This considers the situation where, in the case of the emergency degree at the high level as well, the user may select the emergency consultation because emergency transportation late at night can bother the neighbors, for example.

Preferably the information terminal includes a positioning device configured to obtain positioning information of the information terminal. When the emergency degree is determined as a level lower by one than the high level, the information terminal then functions as a search means configured to search for nearby medical institutions from a medical-institution database on locations and contact numbers of medical institutions based on the positioning information, and display a result of the searching on the display. With this configuration, when the emergency degree is determined as a level lower by one than the high level, the information terminal can search for nearby medical institutions based on the positioning information from the positioning device, such as GPS (Global Positioning System), that the information terminal typically includes internally, and can display information on at least their contact numbers. Thereby the user can contact the medical institutions as needed. The nearby medical institutions may be displayed in the order of proximity based on the positional information on the medical institutions and the positioning information, which facilitates user's selection.

Preferably when the user does not press the emergency calling button, then the information terminal functions as a questionnaire processing means to conduct questionnaire after the case about whether the user visited a medical institution or not and about the history of the medical care. With this configuration, when the user does not press the emergency calling button, meaning that the emergency degree is determined as a level lower by one than the high level, and so an ambulance is not requested, information from the fire department and the medical institutions cannot be obtained in this case. In such a case, questionnaire is conducted after the case about whether the user visited a medical institution later and about the medical care. This can collect information on more emergency cases.

The present invention relating to the program as stated above can be applied similarly to a computer-readable recording medium having stored thereon the program as well.

Preferably an emergency determination supporting system according to the present invention includes: a first server configured to receive, from an information terminal configured to receive, as an emergency case, attribute information on an injured or ill person and information on selected symptoms and determine a level of emergency degree for the received information and equipped with a calling function and a communication function, the attribute information, the received symptoms and information on emergency degree for each emergency case; and a second server configured to, when the information terminal determines the emergency degree as a high level, and when a user makes a call to the emergency calling phone via the calling function for emergency transportation of an injured or ill person, receive pre-hospital activity information including information on the injured or ill person and post-transportation progress information including information on the injured or ill person. One of the first server and the second server includes: a joining means configured to check the attribute information received by the first server against the information on the injured or ill person received by the second server to join the emergency case; and an emergency analysis means configured to statistically evaluate and analyze the relationship between symptoms and the level of emergency degree for each of the joined emergency cases.

An emergency determination supporting method according to the present invention includes: a first reception step in which a first server receives, from an information terminal configured to receive, as an emergency case, attribute information on an injured or ill person and information on selected symptoms and determine a level of emergency degree of the received information, and equipped with a calling function and a communication function, the attribute information, the received symptoms and information on emergency degree for each emergency case; a second reception step in which when the information terminal determines the emergency degree as a high level, and when a user makes a call to the emergency calling phone via the calling function for emergency transportation of an injured or ill person, a second server receives pre-hospital activity information including information on the injured or ill person and post-transportation progress information including information on the injured or ill person; a joining step of checking the attribute information received by the first server against the information on the injured or ill person received by the second server to join each emergency case; and an analysis step of performing statistical evaluation and analysis about the relationship between symptoms and the level of emergency degree for each of the joined emergency cases.

With this configuration, the attribute information on an injured or ill person, information on the selected symptoms and the determined emergency degree from the information terminal can be jointed with the pre-hospital activity information and the post-transportation progress information for each emergency case. Thereby when a symptom is determined as a high-level of emergency by the information terminal, such determination can be evaluated and analyzed based on the medical care performed on the emergency medical service side, and so the appropriateness of the determination can be verified. For instance, although a certain symptom is determined as high-level of emergency by information terminals in a plurality of cases, such a symptom may not be considered as high-level of emergency and the patient may receive the corresponding medical care based on the pre-hospital activity information and the post-transportation progress information. When information on the cases via the emergency consultation phone is fed back later to the second server, the emergency determination can be evaluated also for such cases that are not at a high level in emergency.

Preferably the information terminal includes a positioning device configured to obtain positional information of the information terminal and a time keeping unit configured to obtain time keeping information, and the joining means considers at least one of the positional information and the time keeping information as the attribute information. With this configuration, the information used for checking includes such positional information and time keeping information, whereby the probability and the accuracy for joining improve.

Preferably the system includes a distribution means configured to, when the analyzed relationship by the emergency analysis means between the symptoms and the level of emergency degree is changed, distribute the changed relationship between the symptoms and the level of emergency degree to the information terminal. With this configuration, when the relationship between the symptoms and the level of emergency degree is changed, the changed information can be distributed to each terminal. Therefore the information terminal can determine the emergency degree based on the latest information. The information may be distributed to each information terminal via a network directly. Alternatively this may be via a site selling applications over the network. In this case, the information terminal having the emergency support application downloaded thereon may be registered. This enables updating of the application for the registered information terminal every time the application is updated. Alternatively an updating request is notified to the information terminal, and actual updating may be performed by individuals.

Preferably when the emergency degree is determined as a level lower by one than the high level, the first server receives the result of questionnaire conducted after the case about whether the user visited a medical institution or not and about the history of the medical care through the communication function of the information terminal, and the emergency analysis means creates an emergency case having the relationship between symptoms and levels of emergency degree based on the attribute information, the information on input symptoms and the result of the questionnaire.

Preferably when the emergency degree is determined as a level lower by one than the high level, the method includes a third reception step in which the first server receives the result of questionnaire conducted after the case about whether the user visited a medical institution or not and about the history of the medical care through the communication function of the information terminal, and a creation step of creating an emergency case having the relationship between symptoms and levels of emergency degree based on the attribute information, the information on input symptoms and the result of the questionnaire received by the first server.

Thereby an emergency case having the relationship between symptoms and levels of emergency can be created from the result of the questionnaire. Therefore this can provide a statistical evaluation and analysis about the relationship between symptoms and the level of emergency, for example.

REFERENCE SIGNS LIST

1 Terminal (information terminal)
11 Display
12 Touch panel
13 Positioning device
15 Calling unit
100 Controller
101 Image display processing unit
102 Input reception unit
103 Emergency determination unit
105 Telephone network control unit
106 Search unit
107 Time keeping unit
108 Questionnaire processing unit
2 Management server (first server)
22 Emergency determination log information storage unit
24 Medical institution information storage unit (medical institution database)
202 Joining unit (joining means)
203 Emergency analysis unit
3 Fire department server (second server)
4 Medical institution server (second server)

The invention claimed is:

1. A non-transitory computer readable medium having stored thereon a program that makes an information terminal including a calling unit as well as a display unit, an operating unit and computer execute support for emergency determination, the program making the computer execute:

a symptom selection step of displaying a plurality of symptoms on the display of the information terminal and receiving selection by a user of any symptom from the plurality of symptoms through the operating unit;

an emergency determination step of determining emergency degree corresponding to the symptom selected through the operating unit while referring to a relationship stored beforehand in a storage unit about between symptoms and levels of emergency degree;

an image displaying step of, when the emergency degree is determined as a high level, displaying an emergency calling button on the display;

a telephone network control step of, when receiving user's operation with the emergency calling button on the display making a call via the calling unit to an emergency call phone that is associated beforehand an operation determination step of determining whether the user operates the emergency calling button on the display or not;

a questionnaire asking screen displaying step of, when the user does not operate the emergency calling button, displaying a screen of asking cooperation in questionnaire conducted later on the display, the questionnaire being about whether the user visited a medical institution or history of medical care at the medical institution;

a questionnaire condition determination step of determining, when receiving user's selection to cooperate in the questionnaire via the operating unit, whether a temporal condition for questionnaire is achieved or not by keeping time; and a questionnaire processing step of conducting questionnaire via the operating unit to the information terminal when it is determined that the temporal condition for questionnaire is achieved.

2. The non-transitory computer readable medium according to claim 1, wherein the program further makes the computer execute an injured/ill person information reception step of receiving input of attribute information on an injured or ill person via the operating unit of the information terminal, wherein the emergency determination step determines the emergency degree in accordance with the selected symptom and the attribute information on the injured or ill person.

3. The non-transitory computer readable medium according to claim 1, wherein when the emergency degree is determined as the high level, the image displaying step displays the emergency calling button on the display, and when the emergency degree is determined as a level lower by one than the high level, the image displaying step displays an emergency consultation phone button instead of the emergency calling button on the display, wherein when receiving user's operation with the emergency consultation phone button on the display, the telephone network control step makes a call via the calling unit to an emergency consultation phone that is associated beforehand.

4. The non-transitory computer readable medium according to claim 1, wherein the plurality of symptoms has a plurality of hierarchical levels, and is configured to be a tree form to specify each symptom to be more detailed according to the hierarchical levels, the symptom selection step allows the user to select any symptom at each hierarchical level from an upper level, and the emergency determination step determines the emergency degree in accordance with at least a symptom selected at the lowest hierarchical level.

5. The non-transitory computer readable medium according to claim 1, wherein the information terminal is of a mobile type.

6. The non-transitory computer readable medium according to claim 1, wherein when the emergency degree is determined as a low-level, the image displaying step displays a wait-and-see button on the display.

* * * * *